US011211167B2

(12) United States Patent
Chukka et al.

(10) Patent No.: US 11,211,167 B2
(45) Date of Patent: Dec. 28, 2021

(54) IMAGE ANALYSIS FOR BREAST CANCER PROGNOSIS

(71) Applicants: Ventana Medical Systems, Inc., Tucson, AZ (US); The Cleveland Clinic Foundation, Cleveland, OH (US); The University of Melbourne, Victoria (AU)

(72) Inventors: Srinivas Chukka, San Jose, CA (US); Olcay Sertel, Sunnyvale, CA (US); Anindya Sarkar, Milpitas, CA (US); Nikolaus Wick, Innsbruck (AT); Shalini Singh, Tucson, AZ (US); Crystal Schemp, Tucson, AZ (US); Paul Waring, Melbourne (AU); Raymond Tubbs, Cleveland, OH (US)

(73) Assignees: VENTANA MEDICAL SYSTEMS, INC., Tuscon, AZ (US); THE CLEVELAND CLINIC FOUNDATION, Cleveland, OH (US); THE UNIVERSITY OF MELBOURNE, Victoria (AU)

( * ) Notice: Subject to any disclaimer, the term of this patent is extended or adjusted under 35 U.S.C. 154(b) by 903 days.

(21) Appl. No.: 14/653,831

(22) PCT Filed: Dec. 19, 2013

(86) PCT No.: PCT/EP2013/077295
§ 371 (c)(1),
(2) Date: Jun. 18, 2015

(87) PCT Pub. No.: WO2014/102130
PCT Pub. Date: Jul. 3, 2014

(65) Prior Publication Data
US 2015/0347702 A1 Dec. 3, 2015

Related U.S. Application Data

(60) Provisional application No. 61/747,148, filed on Dec. 28, 2012.

(51) Int. Cl.
*G16H 50/30* (2018.01)
*G16B 30/00* (2019.01)
*G01N 33/574* (2006.01)
*G16H 30/20* (2018.01)

(52) U.S. Cl.
CPC ....... *G16H 50/30* (2018.01); *G01N 33/57415* (2013.01); *G16B 30/00* (2019.02); *G16H 30/20* (2018.01); *G01N 2800/52* (2013.01); *G01N 2800/54* (2013.01)

(58) Field of Classification Search
CPC ............. G06F 19/3431; G06F 19/1922; G06F 19/321; G16H 50/30; G01N 33/57415
See application file for complete search history.

(56) References Cited

U.S. PATENT DOCUMENTS

| 4,444,487 A | 4/1984 | Miller et al. |
|---|---|---|
| 4,745,055 A | 5/1988 | Schenk et al. |
| 6,283,761 B1 | 9/2001 | Joao |
| 9,286,672 B2 * | 3/2016 | Madabhushi ......... G06T 7/0012 |
| 2005/0136549 A1 | 6/2005 | Gholap et al. |
| 2012/0076390 A1 * | 3/2012 | Potts ..................... G06T 7/0014 |
| | | 382/133 |
| 2014/0314286 A1 * | 10/2014 | Madabhushi ......... G06T 7/0012 |
| | | 382/128 |

FOREIGN PATENT DOCUMENTS

| EP | 120694 A2 | 3/1984 |
|---|---|---|
| EP | 125023 A1 | 11/1984 |
| EP | 256654 A2 | 2/1988 |
| JP | 2006511794 A | 4/2006 |
| JP | 2013200287 A | 10/2013 |
| WO | 8803565 A1 | 5/1988 |
| WO | 2004057513 | 7/2004 |

OTHER PUBLICATIONS

Basavanhally et al., Conference Paper in Proceedings/ IEEE International Symposium on Biomedical Engineering. May 2011. Retrieved from the Internet at ieeexplore.ieee.org/abstract/document/5872370 (last accessed Apr. 13, 2018). (Year: 2011).*
Rojo et al. Database Medline, AN 2010114684 (Folia histochemica et cytobiologica, (Jan. 2009) vol. 47, No. 3, pp. 349-354).*
Kayser et al. Database Medline, AN 2010114685 (Folia histochemica etcytobiologica, (Jan. 2009) vol. 47, No. 3, pp. 355-361).*
Isse et al. Database Medline, AN 2012143704 (American journal of transplantation 2012, vol. 12, No. 1, pp. 27-37).*
Barton et al. British Journal of Cancer, 2012, 106, 1760-1765.*
Potts et al. Laboratory Investigation (2012), 1-16.*
Nassar et al. Immunohistochem Mol Morphol, 18 (5), 2010.*
Falkner et al., Nature 298:286, 1982.
Morrison, J. Immunol. 123:793, 1979.

(Continued)

*Primary Examiner* — Michael L Borin
(74) *Attorney, Agent, or Firm* — Charney IP Law LLC; Thomas M. Finetti

(57) ABSTRACT

Heterogeneity for biomarkers in a tissue sample can be calculated. A heterogeneity score can be combined with an immunohistochemistry combination score to provide breast cancer recurrence prognosis. Heterogeneity can be based on percent positivity determinations for a plurality of biomarkers according to how many cells in the sample stain positive. An immunohistochemistry combination score can be calculated. An imaging tool can support a digital pathologist workflow that includes designating fields of view in an image of the tissue sample. Based on the fields of view, a heterogeneity metric can be calculated and combined with an immunohistochemistry combination score to generate a breast cancer recurrence prognosis score.

11 Claims, 24 Drawing Sheets

(56) References Cited

OTHER PUBLICATIONS

Morrison et al., Ann Rev. Immunol 2:239, 1984.
Frankel et al., Mol. Immunol., 16:101-106, 1979.
Cuzick et al., J. Clin. Oncol. 29:4273-8, 2011.
Barton et al., Br. J. Cancer 1-6, Apr. 24, 2012.
Smith and Waterman, Adv. Appl. Math., 2:482, 1981.
Needleman and Wunsch, J. Mol. Biol., 48:443, 1970.
Pearson and Lipman, Proc. Natl. Acad. Sci. USA, 85:2444, 1988.
Higgins and Sharp, Gene, 73:237 244,1988.
Higgins and Sharp, CABIOS, 5:151 153, 1989.
Corpet et al., Nucleic Acids Research, 16:10881 10890, 1988.
Huang, et al., Computer Applications in the Biosciences, 8:155 165, 1992.
Pearson et al., Methods in Molecular Biology, 24:307 331, 1994.
Tatiana Tatusova, et al., FEMS Microbiol. Lett., 174:247 250, 1999.
Altschul et al., J. Mol. Biol., 215:403 410, 1990.
Basavanhally et al., J. Pathol. Info. 2012, 2:1.
Bishop et al, Anal. Quant. Cytol. Histol, 2002, 24:257.
Christiansen et al, ASCO Annual Meeting Proc, 2012, 30.
Davila, et al, Case Rep. Oncol. Jul. 24;3, 2010, 268.
Dowsett, et al, J. Clin. Oncol. 1;26, 2008, 1059.
Potts, et al, Lab. Invest. Sep.;92, 2012, 1342.
International Application No. PCT/EP2013/077295; International Search Report, dated May 28, 2014.
International Application No. PCT/EP2013/077295; Written Opinion, dated May 28, 2014.
Van de Vijver M.J., N Engl J Med. Dec. 19, 2002; 347 (25): 1999-2009.
Dowsett, M, et al.; Steroids, vol. 76, Issue 8, Jul. 2011, pp. 777-780, 10th International Aromatase Conference Proceedings, Sep. 2010.
Vance, G.H., et al.; Arch Pathol Lab Med 133 (2009): 611-612.
Basavanhally, A., et al., Multi-field-of-view strategy for image-based outcome prediction of multi-parametric estrogen receptor-positive breast cancer histopathology: Comparison to Oncotype DX, Journal of Pathology Informatics, 2011, 1-9, 2.
Genomic Health, Oncotype DX Breast Cancer Assay; http://www.oncotypedx.com/ (1 page).
Japanese Office Action dated Sep. 1, 2017 received in corresponding Japanese Patent Application No. 2015-550033.
Mammaprint 70-gene Breast Cancer Recurrence Assay; http://www.agendia.com/healthcare-professionals/breast-cancer (3 pages).
Test ID: FHER2 81954, HERS Amplification Associated with Breast Cancer, FISH, Tissue; http://www.mayomedicallaboratories.com/test-catalog/print/81954.

* cited by examiner

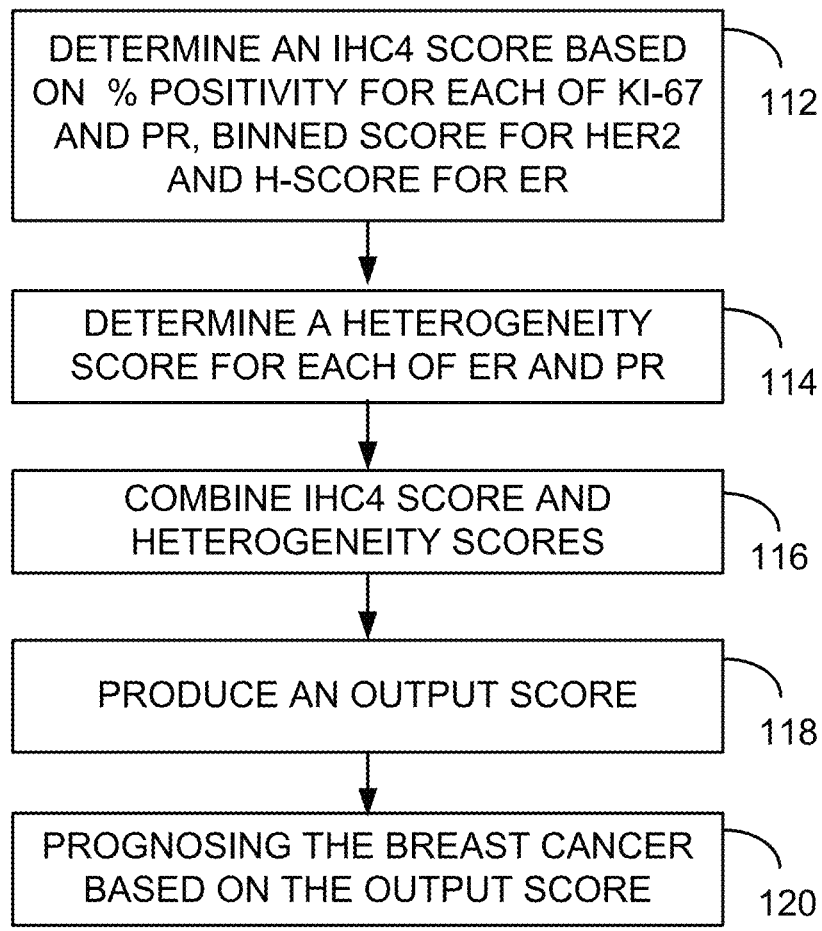

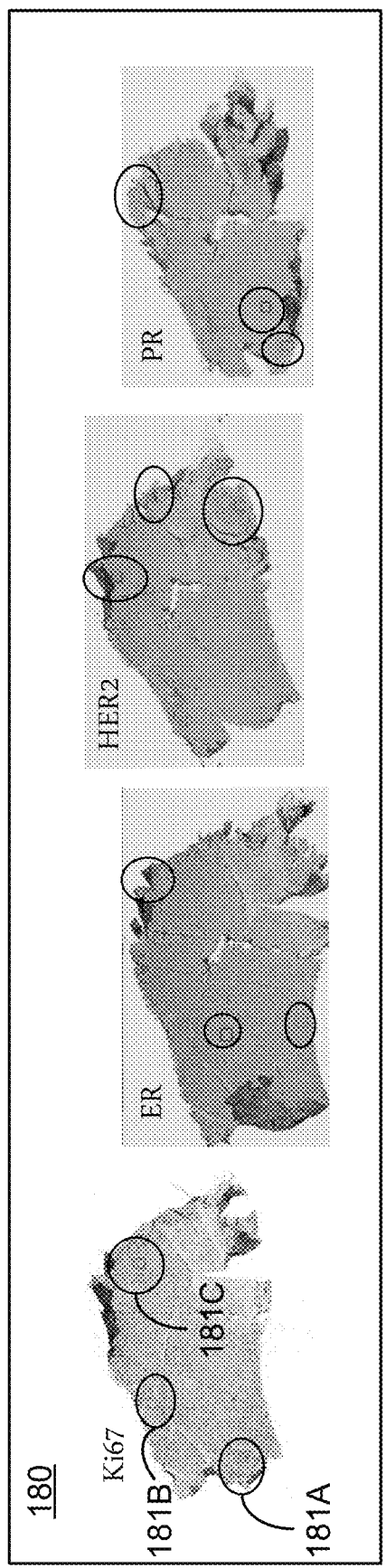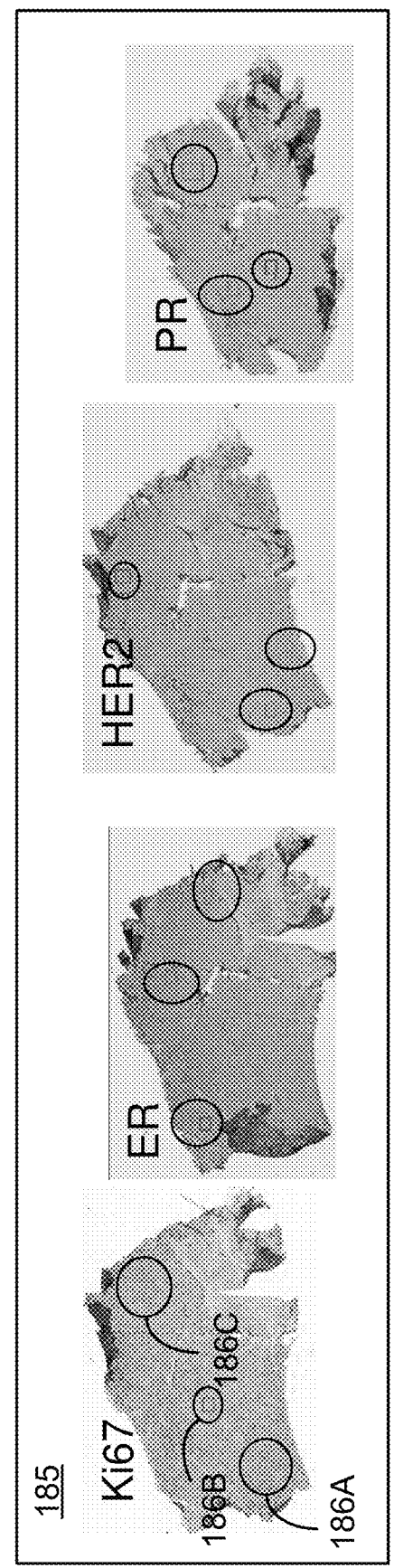

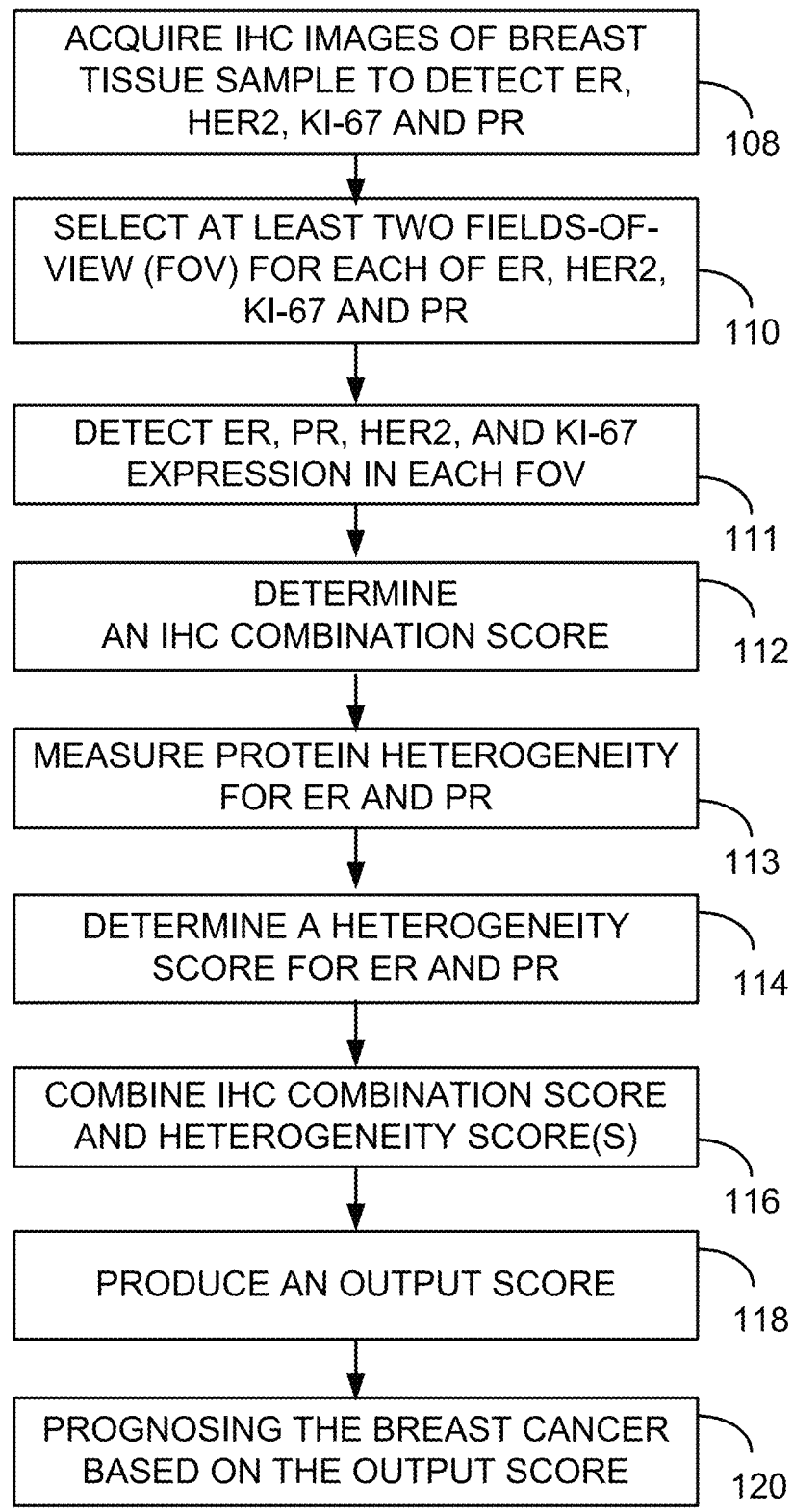

2100

IMAGE ANALYSIS FOR BREAST CANCER PROGNOSIS

This application is a U.S. National Phase application of PCT/EP2013/077295, filed Dec. 19, 2013, entitled "IMAGE ANALYSIS FOR BREAST CANCER PROGNOSIS", which claims the benefit under 35 U.S.C. § 119(e) of and priority to U.S. Provisional Patent Application No. 61/747148, filed Dec. 28, 2012, which is herein incorporated by reference in its entirety.

FIELD

This application relates to image analysis for prognosing breast cancer, such as early stage breast cancer.

PARTIES TO JOINT RESEARCH AGREEMENT

Ventana Medical Systems, Inc., Cleveland Clinic, and the University of Melbourne are parties to joint research agreements governing inventions disclosed herein.

BACKGROUND

Patients with localized (early stage, resectable) breast cancer undergoing curative surgery have an underlying risk of local or distant cancer recurrence, and those people who will recur show an increased mortality rate. Depending on the size of risk, different treatment options exist. Thus, an assay that can reliably identify patients with a low or high risk of cancer recurrence is needed. Accordingly, technologies are also needed that can reliably discriminate between high and low risk patients and provide healthcare providers with additional information to consider when determining a patient's treatment options.

SUMMARY

The present application provides computer-implemented methods for breast cancer prognosis. For example, the method can include generating a breast cancer recurrence prognosis score based at least on measured protein heterogeneity for a biomarker among a plurality of digital fields of view within a displayed image depicting a breast cancer sample detectably labeled with antibodies for the biomarker and an immunohistochemistry combination score for a subject; and outputting an indication of breast cancer recurrence prognosis for the subject based on the breast cancer recurrence prognosis score. Based on these methods, also provided are one or more non-transitory computer-readable media that include computer-executable instructions causing a computing system to perform the disclosed methods.

Also provided are computer-implemented methods. In one example, such methods include a slide image processing tool operable to receive a plurality of slide images depicting protein expression for respective biomarkers in a breast cancer sample from a subject; wherein the slide image processing tool is operable to further receive fields of view within the slide images; wherein the slide image processing tool is operable to calculate an immunohistochemistry combination score based on the slide images and fields of view within the slide images; wherein the slide image processing tool is operable to calculate one or more heterogeneity scores based on the slide images and selections of fields of view within the slide images; and a prognosis tool operable to accept the immunohistochemistry combination score and the one or more heterogeneity scores as input and output an indication of whether cancer is likely to recur in the subject.

The disclosure also provides computer-implemented methods which can include displaying an indication of breast cancer recurrence prognosis. Such methods can include combining an immunohistochemistry combination score and a heterogeneity score into a breast cancer recurrence prognosis score; and displaying an indication of breast cancer recurrence prognosis based on the breast cancer recurrence prognosis score.

Computer-implemented methods are provided that include receiving a plurality of digital fields of view within a displayed image depicting a breast cancer sample detectably labeled with antibodies for a biomarker; measuring protein expression for the biomarker in the digital fields of view; measuring heterogeneity of measured protein expression for the biomarker among the plurality of digital fields of view; and outputting measured protein heterogeneity for the biomarker.

Computer-implemented methods are provided that include calculating an immunohistochemistry combination score for a subject, the method comprising: for a plurality of biomarkers, receiving respective pluralities of digital fields of view within respective images depicting a breast cancer sample detectably labeled with respective biomarker antibodies; measuring percent positivity for a plurality of the biomarkers; calculating the immunohistochemistry combination score, wherein calculating the immunohistochemistry combination score comprises combining the percent positivity for one biomarker with the percent positivity for a second biomarker; and outputting the immunohistochemistry combination score.

Computer-implemented methods are provided that include for ER, receiving a plurality of digital fields of view in an image depicting a breast cancer sample detectably labeled with an antibody for ER; for PR, receiving a plurality of digital fields of view in an image depicting a breast cancer sample detectably labeled with an antibody for ER; for Ki-67, receiving a plurality of digital fields of view in an image depicting a breast cancer sample detectably labeled with an antibody for ER; for HER2, receiving a plurality of digital fields of view in an image depicting a breast cancer sample detectably labeled with an antibody for ER; based on the digital fields of view for ER, calculating an H-score for ER; based on the digital fields of view for PR, calculating a percent positivity for PR; based on the digital fields of view for Ki-67, calculating a percent positivity for Ki-67; based on the digital fields of view for HER2, calculating a binned score for HER2; and combining the H-score for ER, the percent positivity for PR, the percent positivity for Ki-67, and the binned score for HER2 into an immunohistochemistry combination score.

Methods of prognosing or prognosticating breast cancer in a subject are provided. In some examples, such a method includes selecting in a breast cancer sample obtained from the subject at least two different fields of view (FOVs) for each of estrogen receptor (ER), human epidermal growth factor receptor 2 (HER2), Ki-67 and progesterone receptor (PR), wherein the sample is detectably labeled with antibodies for each of ER, HER2, Ki-67 and PR; measuring ER, HER2, Ki-67 and PR protein expression in each of the selected FOV; determining an immunohistochemistry (IHC) combination score; measuring ER and PR protein heterogeneity in each of the selected FOVs; determining a protein heterogeneity score for each of ER and PR; combining the protein heterogeneity score and the IHC combination score, thereby generating an output prognosis score; and determining that the breast cancer in the subject is likely to be aggressive if the output prognosis score meets a threshold value or determining that the breast cancer in the subject is unlikely to be aggressive if the output prognosis score does not meet the threshold value.

Digital fields of view in images of a breast cancer sample from a subject detectably labeled with antibodies for a biomarker can be received and processed to measure protein heterogeneity for the biomarker.

Heterogeneity measurements can be combined with an immunohistochemistry combination score to generate a breast cancer recurrence prognosis score.

Such a score can provide more information than the immunohistochemistry combination score standing alone.

A digital pathologist workflow can be supported to facilitate field of view selection on images.

The foregoing and other objects and features of the disclosure will become more apparent from the following detailed description, which proceeds with reference to the accompanying figures.

BRIEF DESCRIPTION OF THE DRAWINGS

FIG. 3 is a schematic showing an overview of the claimed method.

FIG. 4 A-B are images showing exemplary annotations on fields of view.

FIG. 5 is a schematic showing an overview of the claimed method.

DETAILED DESCRIPTION

Abbreviations and Terms

Figure 1:
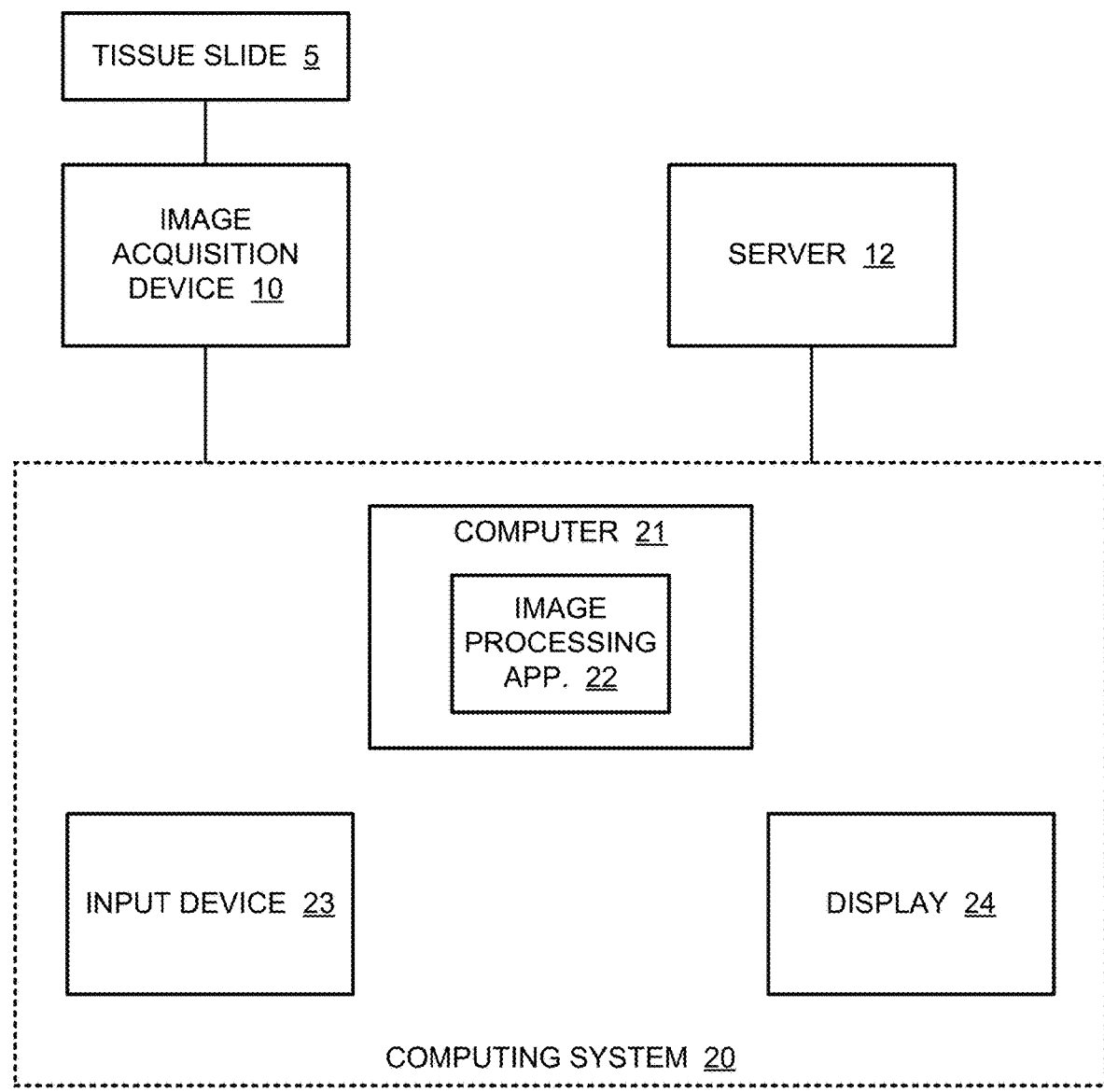
FIG. 1 is a block diagram of an exemplary system for carrying out the technologies described herein.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an antibody" includes single or plural antibodies and is considered equivalent to the phrase "comprising at least one antibody." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank Accession Nos. referred to herein are the sequences available at least as early as Dec. 28, 2012.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Antibody: Immunoglobulin molecules and immunologically active portions of immunoglobulin molecules, that is, molecules that contain an antigen binding site that specifically binds (immunoreacts with) an antigen (such as ER, PR, Ki-67 or HER2). Exemplary antibodies include monoclonal, polyclonal, and humanized antibodies.

A naturally occurring antibody (such as IgG, IgM, IgD) includes four polypeptide chains, two heavy (H) chains and two light (L) chains interconnected by disulfide bonds. As used herein, the term antibody also includes recombinant antibodies produced by expression of a nucleic acid that encodes one or more antibody chains in a cell (for example see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123: 793, 1979; Morrison et al., *Ann Rev. Immunol* 2:239, 1984).

The term antibody also includes an antigen binding fragment of a naturally occurring or recombinant antibody. Specific, non-limiting examples of binding fragments encompassed within the term antibody include Fab, (Fab')$_2$, Fv, and single-chain Fv (scFv). Fab is the fragment that contains a monovalent antigen-binding fragment of an antibody molecule produced by digestion of whole antibody with the enzyme papain to yield an intact light chain and a portion of one heavy chain or equivalently by genetic engineering. Fab' is the fragment of an antibody molecule obtained by treating whole antibody with pepsin, followed by reduction, to yield an intact light chain and a portion of the heavy chain; two Fab' fragments are obtained per antibody molecule. (Fab')$_2$ is the fragment of the antibody obtained by treating whole antibody with the enzyme pepsin without subsequent reduction or equivalently by genetic engineering. F(Ab')$_2$ is a dimer of two FAb' fragments held together by disulfide bonds. Fv is a genetically engineered fragment containing the variable region of the light chain and the variable region of the heavy chain expressed as two chains. Single chain antibody ("SCA") is a genetically engineered molecule containing the variable region of the light chain, the variable region of the heavy chain, linked by a suitable polypeptide linker as a genetically fused single chain molecule. Methods of making these fragments are routine in the art.

Binding affinity: Affinity of an antibody for an antigen, such as the affinity of an antibody for an ER, PR, Ki-67 or HER2 peptide. Methods of determining antibody affinity are known in the art, and include calculation by a modification of the Scatchard method described by Frankel et al., *Mol. Immunol.*, 16:101-106, 1979, measurement by an antigen/antibody dissociation rate, or by a competition radioimmunoassay. A high binding affinity can be at least about $1\times10^{-8}$ M, at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

Breast cancer: Includes any tumor of the breast, such as tumors at, near, or inclusive of epithelial (carcinoma) or stromal (sarcoma) breast tissue. Ductal carcinoma in situ (DCIS) is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al., (eds), Textbook of Breast Cancer: A clinical Guide the Therapy, 3rd; London, Tayloy & Francis, 2006. DCIS is sometimes called Stage 0 breast cancer because it is not invasive. Exemplary invasive breast carcinomas include carcinoma NOS (not otherwise specified), lobular carcinoma, tubular/cribriform carcinoma, mucinous (colloid) carcinoma, medullary carcinoma, papillary carcinoma, and metaplastic carcinoma. An exemplary breast sarcoma is phyllodes tumor.

An early stage breast cancer is one that is stage I or II. A breast tissue sample, for example, that is ER positive, lymph node negative, and, in some examples, HER2 negative may also be characterized as early stage breast cancer. Exemplary therapies for breast cancer include surgery (e.g., removal of some or all of the tumor), hormone blocking therapy (e.g., tamoxifen), radiation, cyclophosphamide plus doxorubicin (Adriamycin), taxane (e.g., docetaxel), and monoclonal antibodies such as trastuzumab (Herceptin) or pertuzumab, or combinations thereof. In some examples, the disclosed methods include administering one or more of these therapies to a subject, such as one identified as having a more aggressive tumor.

Control: A sample or standard used for comparison with an experimental or test sample (such as a breast sample). In some embodiments, the control is a normal sample obtained from a healthy patient (or plurality of patients), such as a normal breast sample or plurality of samples. In some examples, the control is a non-tumor tissue sample obtained from a patient diagnosed with breast cancer, such as normal breast tissue. In some embodiments, the control is a known early stage breast cancer sample (or plurality of samples), such as a sample known to be ER+, PR+, Ki-67+, and HER2−.

In some embodiments, the control is a historical control or standard reference value or range of values (such as a previously tested control sample(s), such as a known breast cancer, normal breast sample, benign breast sample, epithelium, or stroma). In some embodiments the control is a standard value representing the average value (or average range of values) obtained from a plurality of patient samples, such as known normal breast samples or known early breast cancer samples.

Control samples can be used for staining control. Such an approach can be relevant to identifying the signal-to-noise ratio of the sample.

Contact: To bring one agent into close proximity to another agent, thereby permitting the agents to interact. For example, an antibody can be applied to a microscope slide or other surface containing a biological sample, thereby permitting detection of proteins in the sample that are specifically recognized by the antibody.

Detect: To determine if an agent is present or absent, and can include determining a pattern. In some examples this can further include quantification. For example, use of an antibody specific for a particular protein (e.g., Ki-67, ER, PR, or HER2) permits detection of the protein in a sample, such as a sample containing breast cancer tissue. In particular examples, an emission signal from a detectable label (such as an increase in the signal if the target is present) is detected.

Detection can be in bulk, so that a macroscopic number of molecules can be observed simultaneously. Detection can also include identification of signals from single molecules using microscopy and such techniques as total internal reflection to reduce background noise.

Estrogen receptor (ER): A member of the nuclear hormone family of intracellular receptors is activated by 17β-estradiol. Estrogen receptors are overexpressed in around 70% of breast cancer cases, referred to as "ER positive" (ER+).

H-Score: An indication of protein expression that weights strongly stained cells more heavily than weakly stained cells. For example, an H-score can indicate the percentage of cells staining weakly (e.g., 1+) plus two times the percentage of cells staining moderately (e.g., 2+) plus three times the percentage of cells staining strongly (e.g., 3+) (for example see Cuzick et al., *J. Clin. Oncol.* 29:4273-8, 2011, incorporated herein by reference) (also see www.pathogenesys.com/html/semi-quantitative_ihc.html). Exemplary H-score calculation techniques are described herein.

Heterogeneity score: An indication of the amount of protein expression heterogeneity of a biomarker in a sample, such as ER, HER2, Ki-67, or PR staining in a breast cancer sample. The heterogeneity score provides a measure of how different one FOV is from another FOV, for the same marker.

Human epidermal growth factor receptor 2 (HER2): A member of the ErbB protein family, which is a proto-oncogene located at the long arm of human chromosome 17(17q11.2-q12). Approximately 25-30% of breast cancers have an amplification of the HER2/neu gene or overexpression of its protein product, referred to as "HER2 positive"

(HER2+). HER2+ patients can receive the monoclonal antibody trastuzumab (Herceptin) as a therapy for breast cancer, and in some examples is used in combination with the monoclonal antibody Pertuzumab. Overexpression of HER2 in breast cancer has been associated with increased disease recurrence and a worse prognosis.

Immunohistochemistry (IHC) combination score: A prognostic score based on a number of IHC markers, wherein the number of markers is greater than one. IHC4 is one such score based on four measured IHC markers, namely ER, HER2, Ki-67, and PR in a breast cancer sample (for example see Cuzick et al., *J. Clin. Oncol.* 29:4273-8, 2011, and Barton et al., *Br. J. Cancer* 1-6, Apr. 24, 2012, both herein incorporated by reference). In one example, an IHC4 score is calculated using, for example, the following formula:

$$IHC4=94.7\times\{-0.100ER_{10}-0.079PR_{10}+0.586HER2+ 0.240\ \ln(1+10\times Ki67)\}.$$

One skilled in the art will appreciate that other IHC combination scores (e.g., IHC3, IHC5, or the like) are possible.

Ki-67: A nuclear protein associated with cellular proliferation and ribosomal RNA transcription. Inactivation of antigen Ki-67 leads to inhibition of ribosomal RNA synthesis. Ki-67 is used, for example, as a marker of proliferation.

Label: An agent capable of detection, for example by spectrophotometry, flow cytometry, or microscopy (such as light microscopy). For example, one or more labels can be attached to an antibody, thereby permitting detection of the target protein. Exemplary labels include radioactive isotopes, fluorophores, ligands, chemiluminescent agents, enzymes, and combinations thereof. In one example the label is a quantum dot.

Normal cells or tissue: Non-tumor, non-malignant cells and tissue.

Output Prognosis Score: The result of combining and weighting IHC combination (e.g., IHC4) scores and heterogeneity scores for a subject, from which breast cancer prognosis can be determined.

Progesterone receptor (PR or PgR): An intracellular steroid receptor that specifically binds progesterone. Progesterone receptors are overexpressed in some breast cancer cases, referred to as "PR positive" (PR+).

Prognose: The process of determining the likely outcome of a subject having a disease (e.g., early stage breast cancer) in the absence of additional therapy. In one example, the disclosed methods allow for prognosis of a more aggressive form of an early stage breast cancer if an output prognosis score above a threshold is detected. In contrast, prognosis of a less aggressive form of an early stage breast cancer is prognosed if an output prognosis score below a threshold is detected. For example, the prognosis can relate to predicting future events, such as life expectancy (e.g., likelihood of survival in 1 year, 3 years or 5 years), predicting the likely recurrence (either local or metastatic) of breast cancer (e.g., in 1, 3, or 5 years). The like term "prognosticate" is also used herein.

Quantify: To express as a numerical amount, whether an actual amount or a relative amount.

Sample: A biological specimen that may contain, for example, genomic DNA, RNA (e.g., mRNA), protein, or combinations thereof, obtained from a subject. Examples include, but are not limited to, fine needle aspirate, tissue biopsy, surgical specimen, and autopsy material. In one example, a sample includes breast tissue, such as that obtained during a needle biopsy, lumpectomy, or mastectomy.

Staging cancer: A cancer, such as breast cancer, can be staged to describe the extent or severity of a cancer based on the extent of the original (primary) tumor and the extent of spread in the body. Breast cancer can be staged according to the TNM system (see the AJCC Staging Manual), where T describes the size of the tumor and whether it has invaded nearby tissue, N describes any lymph nodes that are involved, and M describes metastasis (spread of cancer from one body part to another).

The stages are as follows: Stage 0—Carcinoma in situ; Stage I—Tumor (T) does not involve axillary lymph nodes (N); Stage IIA—T 2-5 cm, N negative, or T<2 cm and N positive; Stage IIB—T>5 cm, N negative, or T 2-5 cm and N positive (<4 axillary nodes); Stage IIIA—T>5 cm, N positive, or T 2-5 cm with 4 or more axillary nodes; Stage IIIB—T has penetrated chest wall or skin, and may have spread to <10 axillary N; Stage IIIC—T has >10 axillary N, 1 or more supraclavicular or infraclavicular N, or internal mammary N; and Stage IV—Distant metastasis (M).

Subject: Living multi-cellular vertebrate organisms, a category that includes human and non-human mammals, such as veterinary subjects. In a particular example, a subject is one who had or is suspected of having had breast cancer, such as an early stage breast cancer.

Target molecule: A biomolecule whose detection or measurement is desired, such as a breast cancer marker. Examples of target molecules include ER, PR, Ki-67 and HER2.

Under conditions sufficient for: A phrase that is used to describe any environment that permits the desired activity. An example includes contacting an antibody with a breast cancer sample sufficient to allow detection of one or more target molecules (e.g., ER, PR, HER2, Ki-67) in the sample and can include quantification of one or more target molecules in the sample.

Exemplary System Prognosing Breast Cancer

FIG. 1 is a block diagram of an exemplary system for carrying out the technologies described herein. In the example, an image acquisition device 10, such as a slide scanner (e.g., iScan Coreo of Ventana Medical Systems, Inc. or the like) is operable to accept a slide 5 prepared as described herein and generate an image of the slide 5 for analysis as described herein. In practice, a plurality of slides is used as described herein.

The computing system 20 can include one or more input devices 23, one or more displays 24, and one or more computers 21, which can execute an image processing application or platform as described herein.

Data, such as scanned images, can be stored, for example, remotely at a server 12 and/or within a computer 21. Image acquisition can be separately from (e.g., in a different system, by a different actor, or the like) image processing.

In some implementations, a cloud-based or software-as-a-service scenario can be implemented, in which the image processing application 22 resides partially or wholly outside the computer 21 (e.g., at the server 12 or one or more other servers).

Exemplary Methods of Prognosing Breast Cancer

It is shown herein that breast cancers, for example, early stage breast cancers, can be prognosed based on obtaining an immunohistochemistry (IHC) combination score (such as an IHC4) score and/or a heterogeneity score. These two scores are combined and weighted, resulting in an output prognosis score. The resulting output prognosis score can be used to prognosticate the patient with breast cancer. For example, if the output prognosis score is above a threshold value, this indicates that the breast cancer is more aggressive or more likely to recur, while an output prognosis score is below a threshold value indicates that the breast cancer is less aggressive and less likely to recur. This allows clinicians and patients the ability to make more appropriate treatment and monitoring decisions. For example, the output prognosis may be beneficial in determining an appropriate therapy (e.g., choosing between monitoring, a mastectomy, lumpectomy, or a lumpectomy combined with chemotherapy).

Provided herein are methods of prognosing breast cancer, such as early stage breast cancer, in a subject. In some examples, the breast cancer is known to be estrogen receptor positive (ER+), progesterone receptor positive (PR+), and human epidermal growth factor receptor 2 negative (HER2−) or human epidermal growth factor receptor 2 positive (HER2+). For example, the methods can be used to determine the likely aggressiveness of the cancer, or the likelihood that the cancer will recur, for example the likelihood that the cancer will recur within 5 years.

Technologies herein can generate an IHC combination score and a heterogeneity score based on indicated fields of view on images of one or more slides having breast cancer tissue taken from a subject. The scores can then be combined to generate a prognosis score as described herein. Various intermediary calculations and/or scores can be generated before arriving at the IHC combination score or heterogeneity score as described herein.

In an exemplary method, a breast cancer tissue sample is taken from a subject. In some examples, the breast cancer sample is an early stage breast cancer sample, such as one that is HER2 negative (e.g., IHC staining less than 2+ as described herein) and/or FISH amplified, ER positive, and/or lymph node negative. Thus, a HER2 negative sample can be one that (1) shows some IHC staining, such as staining that is less than 2+ or an H-score of <1, or (2) is amplified as indicated by FISH analysis, but is one a clinician or a pathologist would conclude was HER2 negative anyway. The sample may, alternatively, be HER2 positive.

In addition to FISH, other types of in situ hybridization (ISH) can be used, such as chromogenic in situ hybridization (CISH), dual color chromogenic in situ hybridization (DISH), or the like.

Figure 2:
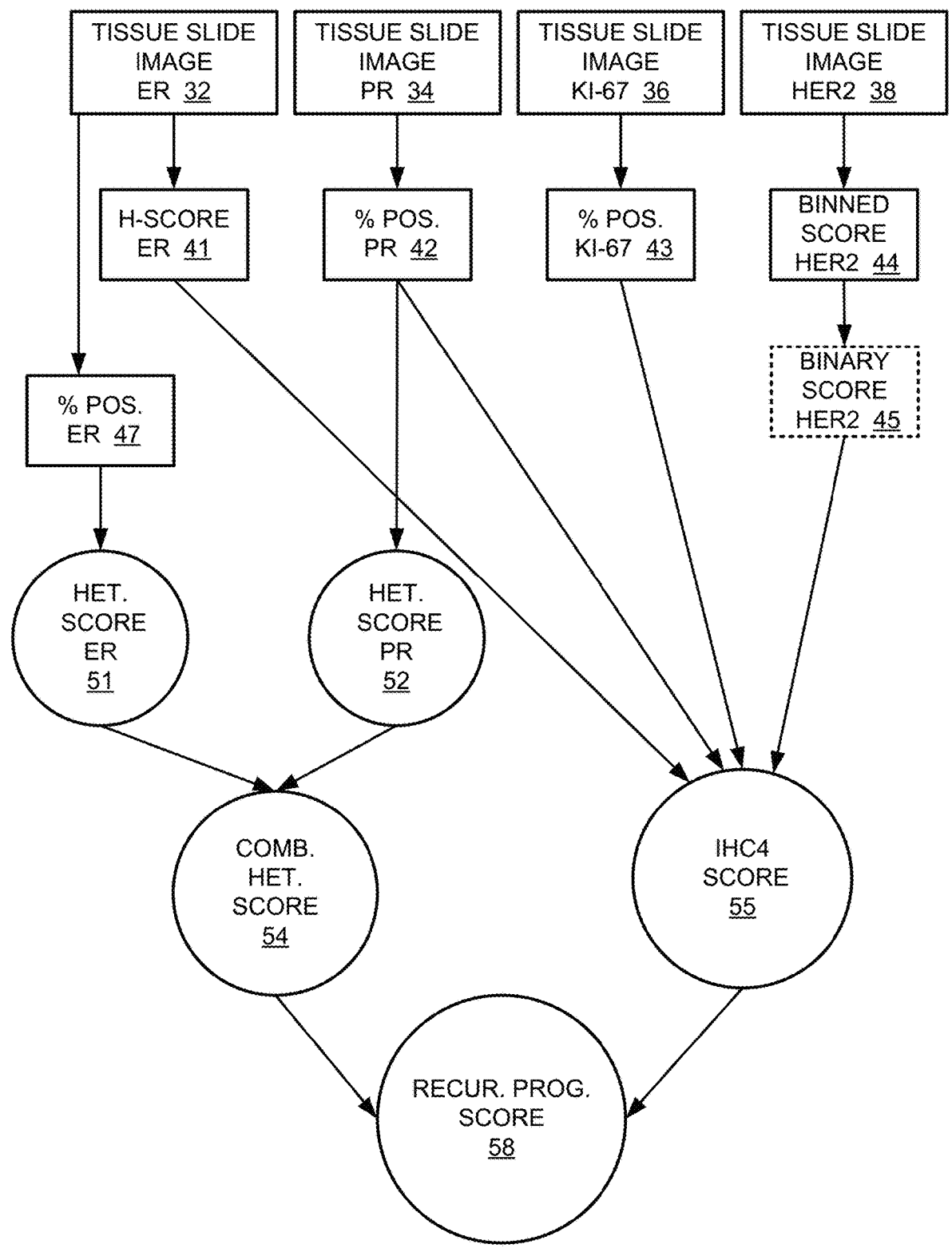
FIG. 2 is a block diagram showing how images of slides stained for different proteins are used to generate a breast cancer recurrence prognosis score.

FIG. 2 is a block diagram showing how images 32, 34, 36, and 38 of slides stained for different proteins are used to generate a breast cancer recurrence prognosis score 58. Although different slides are shown, a tissue microarray approach as described herein can be employed, resulting in fewer slides. For example, a single slide can include a plurality of different tissue sections, which can each be analyzed for a different protein. In another example, a single tissue section, can be analyzed for a plurality of proteins. A sample, for example a tissue block, is divided into sections, for example, four sections, which may or may not be adjacent or serial sections from the sample. Agents specific for the biomarkers of interest, for example, probes or stains, are applied to each section. In one example, an agent specific for the estrogen receptor ER is applied to one section, an agent specific for the PR applied to another section, and the like. Exemplary agents include antibodies and aptamers. Thus, the sample can be detectably labeled with antibodies specific for each of ER, HER2, Ki-67, and PR. Images 32, 24, 36, and 38 of the sample sections are then acquired as described herein. From the images 32, 34, 36, and 38, an H-score for ER 41, a percent positivity for PR 42, a percent positivity for Ki-67 43, and a binned score for HER2 44 are calculated. The binned score 44 can be converted into a binary score (e.g., 0 or 1) 45. The scores are then combined as described herein to generate an IHC4 score 55.

The heterogeneity score for ER 51 relies on a percent positivity determination for ER 47, and the heterogeneity score for PR 52 relies on a percent positivity determination for PR 42. The heterogeneity scores 51 and 52 can be combined as described herein to generate a combined heterogeneity score 54.

The IHC4 score 55 and the combined heterogeneity score 54 can then be combined to generate a breast cancer recurrence prognosis score 58.

FIG. 3 provides an overview of an exemplary method. The method includes determining an IHC4 score via measured expression for each of ER, Ki-67, PR, and HER2 112, for example by determining or measuring a percent positivity for each of PR and Ki-67, a binned score for HER2 (for example on a typical 0 to 3 scale to represent the intensity, wherein 0 is assigned to negative staining, 3 being assigned to very intensely stained samples), and an H-score for ER. The method also includes determining a heterogeneity score for at least ER and PR, and in some examples also Ki-67 and HER2 114. The resulting IHC4 score 112 and heterogeneity score 114, are combined 116 to produce an output prognosis score 118. Based on the output prognosis score, the breast cancer is prognosed 120.

In one example, each slide is scanned, and a digital image is generated of each slide using any of the systems described herein. An IHC combination score is generated by a computer-implemented method based on the slides, and a heterogeneity score is generated for each slide (or section of the slide being analyzed, such as a region containing a tissue section for ER analysis). In an exemplary embodiment, the IHC combination score is referred to as the "IHC4 score," as four biomarkers are utilized to capture information. The IHC4 score can be combined with the heterogeneity scores as described herein to generate a breast cancer recurrence prognosis score.

In one example, to calculate the IHC4 score, the method includes selecting, in the image of each of the tissue section on one or more slides from the breast cancer sample that has been labeled with an agent (such as an antibody), at least two different fields of view (FOV) for each of an ER tissue section slide image, a HER2 tissue section slide image, a Ki-67 tissue section slide image, and a PR tissue section slide image. In an exemplary embodiment of the invention, three (3) FOVs are selected, for each slide or section, to compute the IHC4 score. Tumorous regions are chosen as fields of view.

FIG. 4A shows an exemplary set of slide images 180 and annotations by which fields of view (FOV) 181A, 181B, and 181C are selected (e.g., by a pathologist) on respective of the slide images for calculating an IHC combination score. As shown, the annotations can be independent with no relation between fields of view from one biomarker to the other. In the examples, the fields of view are rectangular. However, as described herein, other techniques can be used (e.g., the fields of view can be other known shapes or irregular shapes). In some examples, the field of view is an area of interest, such as an anatomic region of interest (e.g., gland). In one example, the field of view is a whole slide or whole tissue section.

Based on the fields of view, an IHC combination score is calculated. When calculating components for the IHC combination score, the fields of view can be taken together (e.g., combined and/or considered collectively) for a particular biomarker. For example, H-score, percent positivity, and HER2 binned score can be based on respective sets of fields of view taken together (e.g., the H-score for ER is based on the cells observed in the fields of view). Other techniques are possible (e.g., averaging scores, voting for a score, or the like).

For example, the IHC combination score can be calculated using Dowsett's IHC4 formula or a variation thereof:

IHC4=94.7×{−0.100$ER_{10}$−0.079$PR_{10}$+0.586HER2+ 0.240 ln(1+10×Ki67)}, wherein $ER_{10}$ is the H-score/30 for ER, wherein $PR_{10}$ is obtained by dividing the percentage of cells staining positive (e.g., with an upper limit of 10% imposed on the percentage of cells) by 10 to generate a variable with a range of 0 to 10, wherein HER2 is the binary HER2 score (e.g., 0 if less than 2+, 1 otherwise), and Ki67 is the percent positivity for Ki-67. In practice, $ER_{10}$ is scaled to a 0-10 range by dividing the H-score by 30 as shown in the formula.

For some of the fields of view, nuclei that are stained positive are differentiated from the nuclei that are stained negatively (e.g., not stained) in each field of view. Then, for the PR and Ki-67 slides, the percent positivity is calculated (e.g., the total number of nuclei of cells (e.g., malignant cells) that are stained positive in each field of view in the digital image of a slide are summed and divided by the total number of positively and negatively stained nuclei from each of the fields of view of a digital image) in a single slide as follows:

Percent positivity=number of positively stained cells/ (number of positively stained cells+number of negatively stained cells)

In an exemplary embodiment, the percent positively is determined manually (e.g., without the use of a digital image, with the use of image analysis, or various other image analysis methods.

In an exemplary embodiment, nuclei are detected and classified as positively stained nuclei or negatively stained nuclei via the nuclei identification techniques described herein. For example, negatively stained cells can be differentiated from, for example, lymphocytes and stromal tissue. Such a technique can be superior to using a universal color threshold.

Additionally, the H-score (which reflects the intensity of the stained cells and the number of stained cells for an individual slide) for the ER slide (or tissue section) is calculated, for example. Such a score can be based on the FOVs taken together collectively. In exemplary embodiments, a numerical scale (e.g., 0-300) is used for the H-score. For cells (e.g., in the fields of view) that have been positively stained, the intensity is determined. Such intensity can be determined via an algorithm, compared to a threshold, and assigned a bin number. Such a bin number can be for example, 0, 1, 2, or 3. As a result, there will be a count of nuclei (i.e., cells) in each bin. The bin counts can be used to calculate the H-score.

The intermediate step of binning the nuclei can be re-used later when calculating a heterogeneity score. The positive (e.g., brown) intensities (e.g., 1, 2, and 3) can be aggregated to determine an overall positively stained nucleus count as needed (e.g., for the heterogeneity score for ER).

The calculation of the binary score for HER2 can include determining the binned score (which is related to the completeness of the cell membrane staining and the intensity of stained cell membrane) for the HER2 slide (e.g., based on the fields of view). The binned score for the combined FOVs will be a 0, 1, 2, or 3 as described herein. 0 or 1 are considered negative (0 for the binary score), and 2 or 3 are considered positive (1 for the binary score). Thus, a binary score is calculated for HER2. Alternatively, scores for the FOVs can be combined (e.g., averaged, average and rounded, or the like) to determine an overall score for HER2.

The IHC4 score can then be determined by utilizing the percent positivity, H-score, and binary score described above. ER, HER2, Ki-67 and PR protein expression can be detected or measured in each of the selected FOVs to assist in making these determinations. For example, protein expression can be examined or measured to determine or measure a percent positivity for each of Ki-67 and PR, a binned stain intensity score for HER2, and an H-score for ER. Based on this information, an immunohistochemistry (IHC) combination score can be determined or calculated according to the formula above.

Aside from the collective IHC (e.g., IHC4) combination score for the sample, heterogeneity, for example protein expression heterogeneity, can also be calculated for respective biomarkers (e.g., ER, PER, HER2, and Ki67). Heterogeneity determinations add prognostic value to the already existing value of the IHC combination (e.g., IHC4) score. In an exemplary embodiment, heterogeneity, for example, regional heterogeneity is determined for each biomarker (e.g., ER, PER, HER2, and Ki67). FIG. 4B an exemplary set of slide images 185 showing annotations by which fields of view 186A, 186B, and 186C are selected (e.g., by a pathologist) on respective of the slide images for calculating a heterogeneity score. As shown, the annotations can be independent with no relation between fields of view from one biomarker to the other. A different set of annotations can be used for heterogeneity than those used for the IHC combination score. In some cases, there can be partial overlap between the FOV used for the IHC combination score and the FOV used for the heterogeneity scores (e.g., a field of view can be shared between them for a biomarker).

In an exemplary embodiment, the heterogeneity is determined for a slide (or tissue section) to measure how different the various tumorous regions are from a reference, for example, each other. In an exemplary embodiment, a pathologist selects a number of fields of view for a slide (or tissue section). In an embodiment, the pathologist selects three fields of view, each including tumorous regions with, for example, different percent positivities.

ER and PR protein heterogeneity is measured or detected using the indicated FOVs. For example, measuring protein heterogeneity can include determining a variability metric (VM) for each of ER, and PR, wherein VM=STD(PP($FS_1$), PP($FS_2$), . . . PP($FS_N$)). PP(FS) is the percent positivity for each FOV, FS (e.g., the fields of view of a digital image of a tissue sample that has been contacted with an agent specific for ER probe, an agent specific for PR, or the like). Based on the variability metric, a heterogeneity score for each of ER and PR is determined or calculated. For example, the heterogeneity score for each of ER and PR can be calculated using the following formula, where α=[0,1] (e.g., a number ranging from 0 to 1) is a normalization factor, and S is an average percent positivity slide score as described herein:

$$H = \begin{cases} \alpha * \dfrac{VM}{0.05}, & S < 10\% \\ \alpha * \dfrac{VM}{S}, & \text{otherwise} \end{cases}$$

Embodiments calculating heterogeneity for Ki-67 can use the same or similar formula as that used for ER and PR. The protein heterogeneity score for HER2, which may be useful in some embodiments, can be calculated using the following formula:

$$H = \sum_{\substack{\forall i,j \\ i \neq j}} \|P(FS_i) - P(FS_j)\|$$

wherein P(FS) is the binned HER2 score (e.g., determined as described herein) for each field of view, FS. If the binned scores for each field of view are equal (e.g., P(FS$_1$)= P(FS$_2$)=P(FS$_N$)), then H=0. H thus indicates how different protein expression is in the different fields of view for a biomarker.

In an exemplary embodiment, at least one of the heterogeneity scores is utilized to determine the output prognosis score. In an embodiment, the resulting heterogeneity scores for respective of the slides and the IHC combination score are combined and weighted, thereby generating an output prognosis score. In an exemplary embodiment, the output prognosis score is a factor or percentage (P1) times the IHC combination score plus a factor or percentage (P2) of a combined heterogeneity score, where P1 and P2 are greater than 0. For example, the output prognosis score (PS) can be calculated by using the formula:

PS=0.03114*IHC4+1.95119*combined heterogeneity score where the combined heterogeneity score is equal to the square root (ER heterogeneity score+PR heterogeneity score). The resulting output prognosis score if used to determine the prognosis of the patient having the breast cancer. For example, the method can prognosticate that the breast cancer in the subject is likely to be aggressive or recur (e.g., within 5 years) if the output prognosis score is above a certain threshold or that the breast cancer in the subject is unlikely to be aggressive or recur if the output prognosis score is below the threshold.

In some examples, the method can include obtaining a digitized image of the breast cancer sample (for example one that is on one or more microscope slides) that is detectably labeled for each of ER, HER2, Ki-67 and PR. For example, one or more digitized images can be obtained for each of ER, HER2, Ki-67 and PR. In some examples, the method further includes selecting a subject prognosed as having a higher likelihood of recurrence, for example selecting the patient for more aggressive therapy.

FIG. 5 provides further details on a particular embodiment of a method in accordance with the technology. The method can also include acquiring or obtaining images (such as a digital image) of the breast cancer sample stained to detect ER, HER2, Ki-67, and PR 108. At least two FOV for each of ER, HER2, Ki-67, and PR are selected 110, for example selected and marked on a digital image. However, the number of FOVs selected may vary (e.g., there may be 2, 3, 4, 5, 6, 7, 8, 9 or 10 FOVs). After selecting the FOVs 110, the method includes detecting or measuring ER, HER2, Ki-67, and PR expression in each FOV 111. Based on this information, an IHC (e.g., IHC4) score is determined via the expression for each of ER, Ki-67, PR, and Her2 112, for example by determining or measuring a percent positivity for each of PR, and Ki-67, a binary score based on a binned score for HER2 (for example on a typical 0 to 3 scale to represent the intensity, wherein 0 is assigned to negative staining, 3 being assigned to very intensely staining samples), and an H-score for ER. The method also includes detecting or measuring protein heterogeneity for each of ER and PR, and in some examples also Ki-67 and HER2 113. Based on this information, a heterogeneity score for at least ER and PR, and in some examples also Ki-67 and HER2, is determined 114. The resulting IHC4 score 112 and heterogeneity score 114, are combined to produce an output prognosis score 118. Based on the output prognosis score, the breast cancer is prognosed 120.

Figure 6:
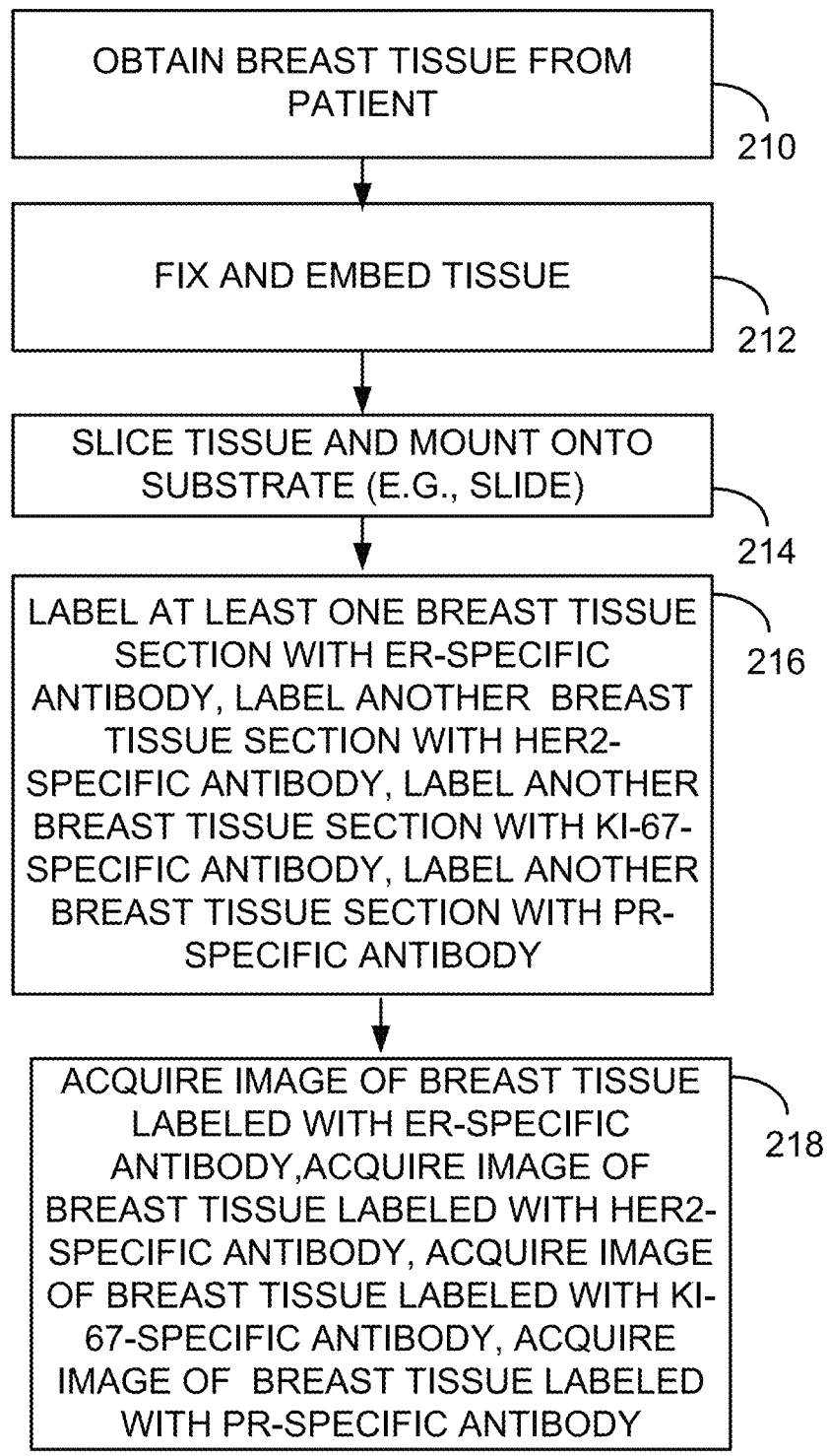
FIG. 6 is a schematic drawing showing exemplary steps of obtaining immunohistochemistry (IHC) images of a breast tissue sample.

FIG. 6 provides details on an exemplary method for obtaining or acquiring the IHC images of the breast tissue sample that is analyzed using the methods provided herein. Methods of obtaining and staining samples are routine in the art. For example, the method can include obtaining the breast tissue from a patient 210, for example from a breast biopsy. The resulting tissue is then fixed and embedded 212, for example using formalin and paraffin. The fixed and embedded tissue can then be sliced or sectioned and mounted onto a substrate 214, for example mounted onto one or more glass microscope slides. In some examples, one slide includes a plurality of tissue sections, such as at least 2 or at least 4 sections. The tissue sections can then be incubated with appropriate antibodies (or other specific binding agents) to label ER, HER2, Ki-67, and PR proteins. For example, at least one breast tissue section can be labeled with an ER-specific antibody, another breast tissue section can be labeled with a HER2 specific antibody, another breast tissue section can be labeled with a PR specific antibody, and another breast tissue section can be labeled with a Ki-67 specific antibody 216. However, one skilled in the art will appreciate that a single tissue section can be labeled with more than one antibody (or other specific binding agent), as long as such labeled proteins are distinguishable, for example by using differently labeled-secondary antibodies. After labeling the tissue sections, images can be obtained. For example, one or more images of the breast tissue section labeled with the ER-specific antibody can be obtained, one or more images of the breast tissue section labeled with the HER2-specific antibody can be obtained, one or more images of the breast tissue section labeled with the PR-specific antibody can be obtained, and one or more images of the breast tissue section labeled with the Ki-67-specific antibody can be obtained 218.

Figure 7:
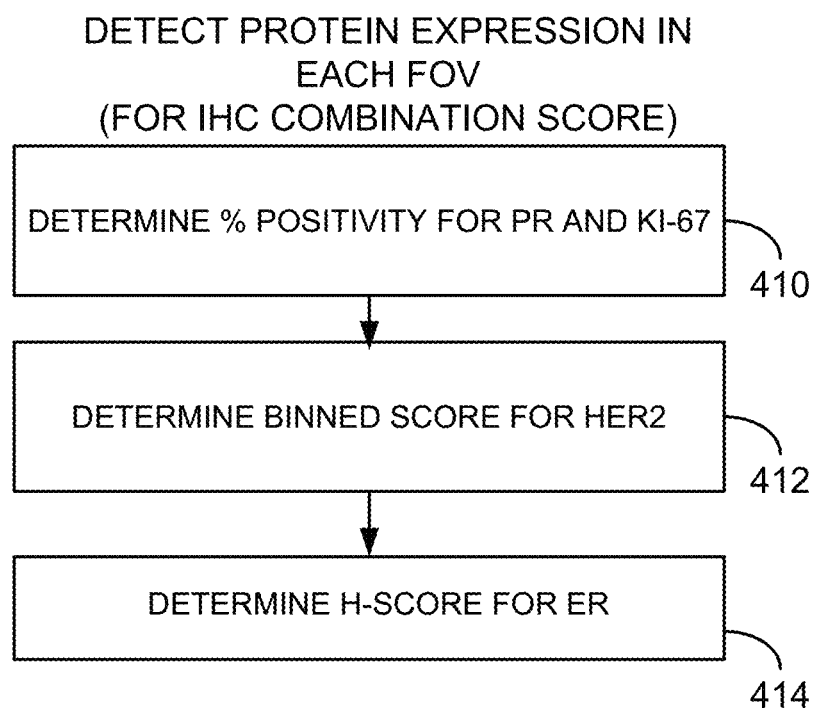
FIG. 7 is a schematic drawing showing exemplary steps of determining or measuring protein expression in a field of view.

FIG. 7 provides details on parameters that can be measured or determined when detecting protein expression in each FOV. Such values can be used to calculate the IHC (e.g., IHC4) score. As noted in FIG. 5, after selecting the FOVs 110, the method includes detecting or measuring ER, HER2, Ki-67, and PR expression in each FOV 111. As shown in FIG. 7, detecting protein expression in each FOV can include determining or measuring a percent positivity for each of PR, and Ki-67 410, determining or measuring a binned score for HER2 412 as described herein, and determining or measuring an H-score for ER 414. The scores can be combined into an immunohistochemistry score as described herein. Combining can comprise converting the binned score for HER2 into a binary score for HER2.

Figure 8:
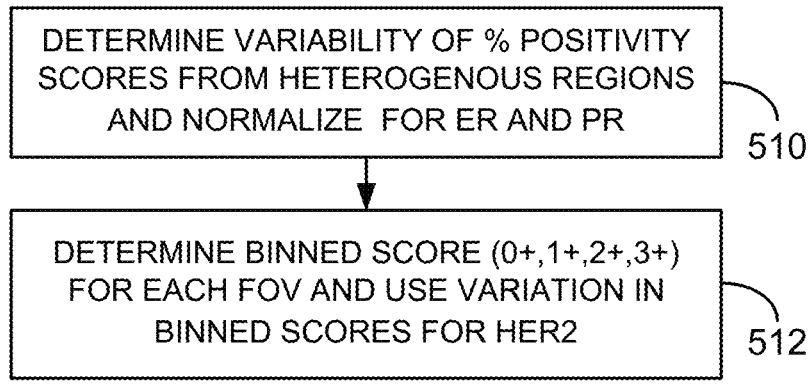
FIG. 8 is a schematic drawing showing exemplary steps of determining or measuring protein heterogeneity.

FIG. 8 provides details on parameters that can be measured or determined when measuring protein heterogeneity in each FOV. Such values can be used to calculate the heterogeneity score. As noted in FIG. 5, the method can include detecting or measuring protein heterogeneity for each of ER, HER2, Ki-67, and PR 113. As shown in FIG. 8, detecting protein heterogeneity can include determining or measuring the variability of percent positivity in each FOV and normalizing the values, for at least ER and PR (and in some examples also Ki-67) 510. For example, a variability metric (VM) for each of ER and PR (and in some examples Ki-67) is calculated, wherein VM=STD(PP(FS$_1$), PP(FS$_2$), . . . PP(FS$_N$)), and PP(FS) is the percent positivity for each field of view, FS. As shown in FIG. 8, measuring protein heterogeneity for HER2 can include determining or measuring the binned score for each FOV for HER2 and variation between binned scores 512 (e.g., using the binned score determined in 412 above, but incorporating at least one other FOV).

Exemplary System Implementing the Technologies

Figure 9:
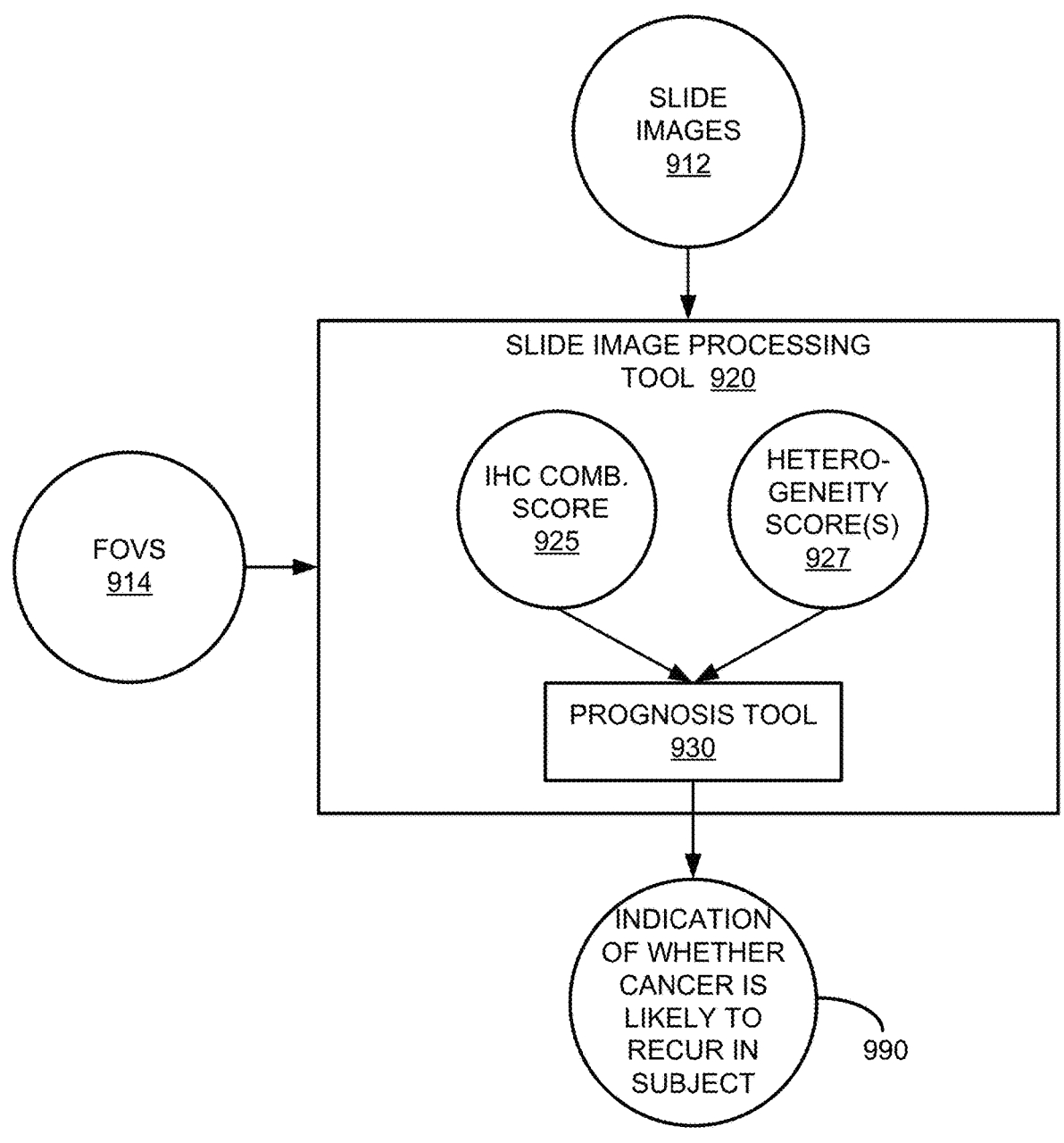
FIG. 9 is a block diagram of an exemplary system implementing the breast cancer prognosis technologies described herein.

FIG. 9 is a block diagram of an exemplary system 900 implementing the breast cancer prognosis technologies described herein. In the example, a slide image processing tool 920 can accept a plurality of slide images 912 and a plurality of fields of view 914 as input. The tool 920 outputs an indication 990 of whether cancer is likely to recur in the subject. As described herein, such an indication 990 can be based on an output prognosis score.

The slides can depict protein expression for respective biomarkers in a breast cancer sample from a subject (e.g., detectably labeled with antibodies for the biomarkers as described herein).

The tool 920 can provide user interfaces for receiving selections of the fields of view (FOV) 914 or such functionality can be provided by another tool or component.

The IHC combination score can be calculated (e.g., by the tool 920 or another tool or component) based on the slide images and fields of view within the slide images.

The tool 920 is operable to calculate one or more heterogeneity scores 927 based on the slide images and fields of view within the slide images as described herein.

The slide image processing tool 920 can include a prognosis tool 930 that accepts a calculated IHC combination score and the one or more heterogeneity scores 927 as input and outputs an indication 990 of whether cancer is more aggressive, and thus more likely to recur in the subject.

In practice, the systems shown herein, such as system 900 can be more complicated, with additional functionality, more complex inputs, and the like. For example, additional functionality can compute the IHC combination score, the heterogeneity score(s), or both, or such scores can be provided by other software.

The system 900 and any of the other systems described herein can be implemented in conjunction with any of the hardware components described herein, such as the computing systems described below (e.g., processing units, memory, and the like). In any of the examples herein, the inputs, outputs, and tools can be stored in one or more computer-readable storage media or computer-readable storage devices. The technologies described herein can be generic to the specifics of operating systems or hardware and can be applied in any variety of environments to take advantage of the described features.

Exemplary Computer-Implemented Method Implementing the Technologies

Figure 10:
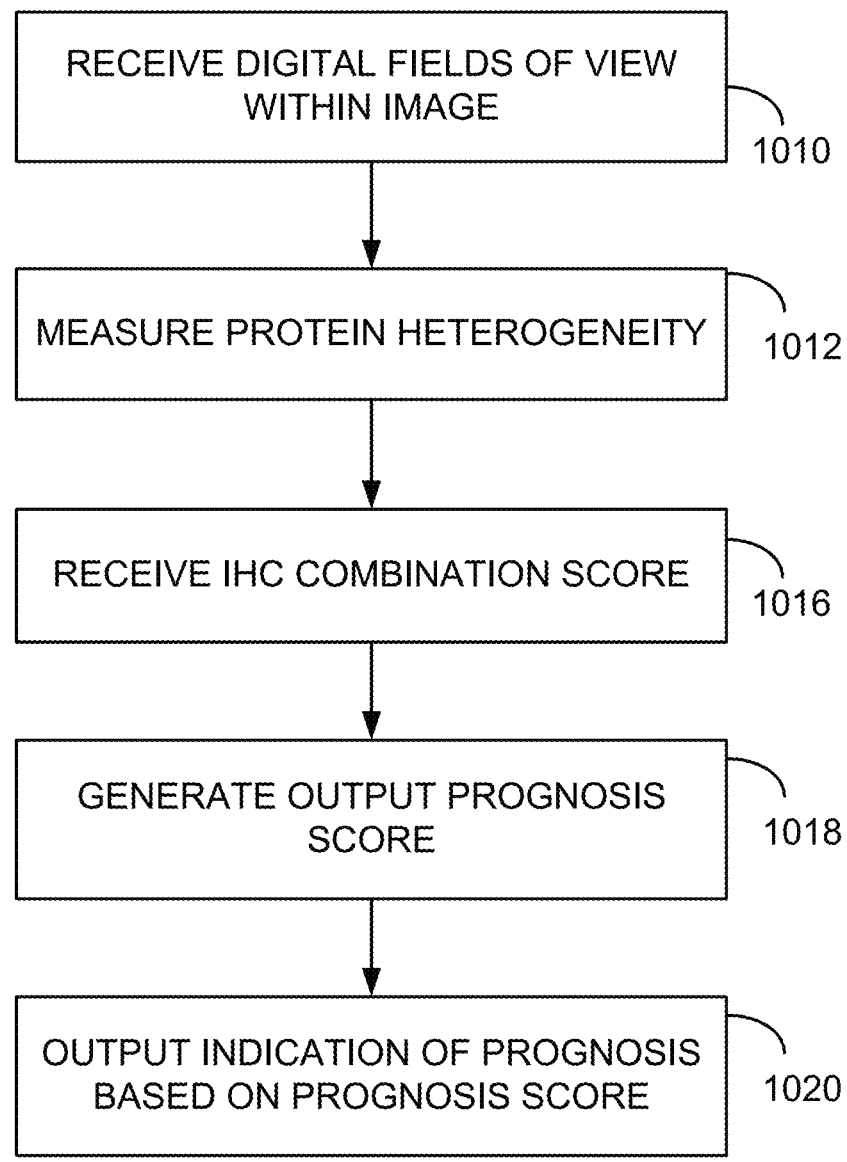
FIG. 10 is a flowchart of an exemplary computer-implemented method implementing the breast cancer prognosis technologies described herein.

FIG. 10 is a flowchart of an exemplary computer-implemented method 1000 implementing the breast cancer prognosis technologies described herein and can be implemented, for example, in the system shown in FIG. 9.

The method can be performed on one or more slide input images that are received for processing. For example, a slide image depicting a breast cancer sample from a subject detectably labeled with antibodies for a biomarker as described herein can be used.

At 1010, a plurality of digital fields of view are received within an image. As described herein, an indication of a field of view can be received via selections of displayed images (e.g., by tracing an outline on the image for a field of view) or an indication of a boundary within an image.

At 1012, protein heterogeneity is measured among the digital fields of view as described herein (e.g., interregional heterogeneity is determined for the fields of view for a given slide image). For example, protein expression for a biomarker can be measured for the respective fields of view, and the measurements compared for variability as described herein. In practice, heterogeneity can be measured for a plurality of biomarkers (e.g., as a heterogeneity score). One or more of ER, PR, and the like (e.g., Ki-67, HER2, or the like) can be used.

When measuring protein heterogeneity for a second biomarker, a second plurality of digital fields of view within a displayed image depicting a breast cancer sample from the subject detectably labeled with antibodies for a second biomarker can be received. Protein heterogeneity for the second biomarker can be measured (e.g., as a separate heterogeneity score from the first).

At 1016, an IHC combination score for the subject is received. Any of the IHC combination scores described herein can be supported. The IHC combination score can be for the same sample used for the heterogeneity analysis, or a different sample from the same subject can be used.

At 1018, an output prognosis score is generated based at least on the measured protein heterogeneity for the biomarker among the plurality of digital fields of view and the immunohistochemistry combination score for the subject. As described herein, an IHC combination score and one or more heterogeneity scores for respective biomarkers can be generated and used to calculate an output prognosis score.

At 1020, based on the output prognosis score, an indication of prognosis (e.g., indication 990 of whether cancer is more aggressive and thus likely to recur in the subject) is output. For example, thresholds as described herein can be used to select between or among categories of prognosis indications; indicate a yes or no result; or the like.

The method 1000 and any of the other computer-implemented methods described herein can be performed by computer-executable instructions (e.g., causing a computing system to perform the method) stored in one or more computer-readable media (e.g., storage or other tangible media) or stored in one or more computer-readable storage devices.

Exemplary Receiving of Field of View

In any of the examples herein, a field of view can be received as a stored indication of an area (e.g., a set of pixels, a boundary, or the like) within an image or as an annotation (e.g., drawing, tracing, or the like) by a computer system operated by a pathologist with reference to (e.g., on) an image (e.g., which is then stored for later use).

For example, annotation can be performed by a separate tool or software or incorporated into the tool or software that performs heterogeneity analysis.

Exemplary Immunohistochemistry Combination Score

In any of the examples herein, an immunohistochemistry combination score can be combined with a heterogeneity score to yield a breast cancer recurrence prognosis score. For example, the IHC (e.g., IHC4) score described herein or another immunohistochemistry combination score combining two or more biomarkers, for example, HER2, ER, PR, Ki-67, or the like can be used. Such a score can be determined via the fields of view indicated by a pathologist as described herein.

Heterogeneity can be analyzed for the biomarkers used to generate the IHC combination score as described herein and combined with the IHC combination score to result in an output prognosis score.

Exemplary Image

In any of the examples herein, an image can be a digital image depicting a breast cancer sample from a subject detectably labeled with antibodies for a particular biomarker. In practice, such an image depicts a section of such a sample. Different sections can be used for different biomarkers.

The technologies can support a plurality of images for respective of the biomarkers. Implementations can support multiple biomarkers in a single image (e.g., in a multiplex scenario).

When stored, an image can be represented as image data, pixels or voxels having, for example, color values, intensity values, or both. Image pixel or voxels can be processed as described herein. For example, fields of view within the images can be analyzed to quantify protein expression within the field of view for a given biomarker.

Exemplary Fields of View

In any of the examples herein, a digital field of view can be an area within an image or an indication of such an area and is sometimes simply called a "field of view" herein. Such fields of view can comprise regions of interest as indicated by a pathologist. In some implementations, slides can be compared to other slides, so the field of view can be the entire slide. However, because the field of view is typically smaller than the entire digital image, it typically corresponds to an area that is smaller than the entire section being imaged. In practice, such a digital field of view can be stored as a separate image or indicated by a boundary (e.g., originally drawn by a pathologist and stored electronically) with reference to a reference image (e.g., the image from which the field of view was derived). Portions of the image inside the boundary are considered within the field of view, and portions of the image outside the boundary are considered outside the field of view. Portions on the boundary can be considered inside or outside as desired.

Typically, digital fields of view are contiguous regions of pixels or voxels within the image as selected by a pathologist according to an appropriate protocol. Any arbitrary shape (e.g., rectangular, non-rectangular, square, elliptical, circular, traced shape, or the like) or area of interest can be supported, and tools can be provided for selecting particular shapes (e.g., a tracing tool, an ellipse tool, a circle tool, a square tool, a rectangle tool, or the like). A field of view can comprise an anatomical structure of interest (such as a gland).

Different fields of view are typically selected for immunohistochemistry combination scores and heterogeneity scores; however, it is possible for there to be overlap between the two. In other words, fields of view for an immunohistochemistry combination score can be reused for a heterogeneity score and vice versa.

When storing, receiving, or outputting fields of view, a reference to the digital field of view can be used instead of the actual field of view data itself.

Exemplary Field of View Selection

In any of the examples herein, fields of view can be selected according to a protocol appropriate for the purpose. For example, for those fields of view used in an IHC (e.g., IHC4) score, the protocol specifies that selected fields (e.g., 2, 3, 4, 5, 6, 7, or the like) be tumor regions and be representative (e.g., similar looking) of protein expression of the biomarker within tumor tissue. For those fields of view used for a heterogeneity score, the protocol specifies that fields (e.g., 2, 3, 4, 5, 6, 7, or the like) representing different (e.g., heterogeneous) levels of protein expression of the biomarker within tumor tissue are to be selected. In some cases, a single field can be used for both purposes (e.g., one of the heterogeneous fields is also used in an IHC combination score).

A user interface presented to the selecting user (e.g., a pathologist) can indicate for what purpose the fields of view are being selected and also provide guidance regarding the protocol as appropriate.

Exemplary Protein Heterogeneity

In any of the examples herein, protein heterogeneity refers to the spatial variation of histochemical and molecular staining patterns, such as the staining patterns for breast cancer biomarkers ER, HER2, Ki-67 and PR in a breast cancer sample and is sometimes called simply "heterogeneity" herein. For example, heterogeneity increases with the variability of level of biomarkers at different locations within a single sample. Heterogeneity can be an indicator of the spatial variation of tumor aggressiveness and/or growth patterns that can be correlated with an aggregated clinical phenotype (e.g., a tumor likely to recur).

It is shown herein that biological heterogeneity of ER and PR protein expression is correlated with the unpredictable recurrence of a fraction of early stage breast cancer patients.

Heterogeneity can be measured by a variability metric measuring how different the protein expression levels among fields of view for the same biomarker are (e.g., the variability of protein expression measurements within fields of view for a single biomarker). Thus, interregional (e.g., inter-FOV) heterogeneity can be used.

A quantitative measure of interregional heterogeneity (e.g., heterogeneity among the fields of view) can be calculated based on a deviation (e.g., standard deviation or other moment of the distribution) of protein expression measurement, PE (e.g., percent positivity), in the different fields of view for a given biomarker (e.g., ER, PR, Ki-67, or the like). Such a measurement can quantify how far apart (e.g., the spread of distribution) protein expression measurements are. For example, an exemplary heterogeneity calculation for a set of fields of view having respective protein expression measurements $PE(FS_1)$, $PE(FS_2)$, ... $PE(FS_N)$ for a given biomarker in fields of view FS can be calculated as follows:

Exemplary Heterogeneity $(H) = \sigma(PE(FS_1), PE(FS_2), \ldots PE(FS_N))$

The value can be normalized according to an average slide score (S), which can be the average of protein expression measurements for a particular slide (e.g., the average of $PE(FS_1)$, $PE(FS_2)$, ... $PE(FS_N)$). If the average slide score (S) is below a threshold (e.g., 10% or the like), a substitute value (e.g., 5%) can be used as the average slide score. Normalization can be achieved by dividing the observed deviation by the average slide score.

For biomarkers involving binned calculations (e.g., HER2), a sum of bin differences between permutations of the fields of view can be used as a measurement of heterogeneity. Heterogeneity can thus be calculated by aggregating binned score differences for different fields of view for the marker. For example, heterogeneity for a set of fields of view (i and j) having respective protein expression binned scores (e.g., 0, 1, 2, 3) $P(FS_1)$, $P(FS_2)$, ... $P(FS_N)$ for a given binned biomarker can be calculated as follows:

$$H = \sum_{\substack{\forall i,j \\ i \neq j}} \|P(FS_i) - P(FS_j)\|$$

In the example, a single field of view has a single binned score. If all the binned scores are equal, the score is 0.

As described herein, normalization can be done according to the biomarker involved.

Exemplary Spatial Protein Heterogeneity

In any of the examples herein, spatial protein heterogeneity can be measured. Such heterogeneity can be categorized as geographical, regional, inter-glandular, intra-glandular, or the like.

For example, geographic heterogeneity can be measured by measuring variation in protein expression at a geographic level: two separate tissue blocks more than a threshold distance (e.g., 2 inches) apart.

Regional heterogeneity can be measured by measuring variation in protein expression at a regional level: in the same tissue section, for example, between 0.25 and 2 inches apart, and different fields of view, for example, at least distance of a 4× objective apart. Fields of view as described herein can be used to measure such regional heterogeneity.

Inter-glandular heterogeneity can be measured by measuring variation in protein expression at an inter-glandular level: for example, less than 0.25 inches apart and within a 4× objective.

Intra-glandular heterogeneity can be measured by measuring variation in protein expression at an intra-glandular level: for example, the formations in a 20× objective for regional and inter-glandular categories.

Exemplary Alternative Heterogeneity Scores

In any of the examples herein, variability metrics (VM) other than standard deviation, σ, can be used to measure inter-region protein heterogeneity. For example, inter-regional differences in protein expression measurements or a maximum thereof (e.g., when more than two fields of view) can be used. For example, an exemplary heterogeneity calculation for a set of fields of view having respective protein expression (PE) measurements for fields of view $FS_1$, $FS_2$, $FS_3$ for a given biomarker can be calculated as follows using an absolute value (ABS) function:

$$VM = MAX(ABS(PE(FS_1) - PE(FS_2)), ABS(PE(FS_1) - PE(FS_3)), ABS(PE(FS_2) - PE(FS_3)))$$

Such a calculation can also account for the range of variability. For example, the minimum inter-regional difference can also be taken into account. An exemplary calculation can thus be:

$$VM_{adj} = VM - MIN(ABS(PE(FS_1) - PE(FS_2)), ABS(PE(FS_1) - PE(FS_3)), ABS(PE(FS_2) - PE(FS_3)))$$

Further variations are possible.

Exemplary Normalization of Heterogeneity Scores

In any of the examples herein, normalization can be applied to heterogeneity scores (e.g., a heterogeneity score for a biomarker). For example, normalization can be achieved by dividing the observed deviation by the average slide score (e.g., for the measured biomarker) as described above.

Further normalization can be achieved based on the given biomarker involved. For example, based on historical observation of the heterogeneity of protein expression for a given biomarker, a coefficient or other normalization technique can be used.

An exemplary heterogeneity calculation for with a normalization factor α (e.g., with range zero to one) for a variability metric VM (e.g., standard deviation or the like) and S (e.g., an average percent positivity slide score) thus can be:

$$H = \begin{cases} \alpha * \dfrac{VM}{0.05}, & S < 10\% \\ \alpha * \dfrac{VM}{S}, & \text{otherwise} \end{cases}$$

A per-biomarker normalization factor, a, can account for differences in impact that heterogeneity of a specific biomarker has on the prognosis score. As data for heterogeneity analysis is seen, such per-biomarker normalization factors can be adapted.

In one example, a was 1.0 for ER and PR, and 0.75 for Ki-67. Such a factor can be determined via statistical methods to determine appropriate weightings for the biomarker(s) involved (e.g., to separate patients into prognosis categories based on the resulting prognosis score).

Exemplary Measurements of Protein Expression

In any of the examples herein, protein expression for a given biomarker can be quantified by measuring a degree to which the protein is expressed (e.g., in a field of view or collectively in fields of view). With reference to stained cells in a field of view, protein expression can be expressed as a percent of the cells in the field of view that are positive stained. For example, a quantification, PP(FS), of protein expression for a field of view, FS, can be calculated to determine percent positivity as follows:

$$PP(FS) = (\text{positively stained cell count in } FS)/(\text{total cell count in } FS)$$

In such a case, the total cell count can be a sum of the positive stained cell count and the negative stained cell count. In practice, a count of the positive stained cells can be determined, a count of the negative stained cells can be determined, and based on the two, the protein expression can be calculated. Because the quantification indicates the percent of cells that are positive stained, such a measurement is sometimes called "percent positivity" for a field of view (e.g., for a given biomarker).

Other techniques can be used to measure protein expression.

A binned score as described herein can be used to measure protein expression (e.g., for HER2).

Exemplary Determination of Percent Positivity

In any of the examples herein, percent positivity for a given field of view can be determined via any number of techniques. The technologies described herein can make use of current and future-developed techniques for determining percent positivity.

Some such techniques count cell nuclei of positive stained cells and count cell nuclei of negative stained cells. Such a technology can filter out stromal and lymphocyte regions of the field of view. If desired, information from an entire slide can be used when counting nuclei.

Thus, protein heterogeneity can be determined by determining percent positivity measurements for respective fields of view for an image associated with a biomarker, where the percent positivity measurements indicate a percent of cells in the respective fields of view that are positive stained for the biomarker. The percent positivity measurements can then be compared as described herein (e.g., to generate a variability metric).

Also, a percent positivity determination can include determining intensity of staining and determining a count of nuclei for a plurality of bins (e.g., 0, 1, 2, 3). Those nuclei in bin 0 can be considered negative, and the others can be aggregated as the positively stained cells. Having such bin information can be useful for other purposes, such as calculating an H-score or the like.

Figure 11:
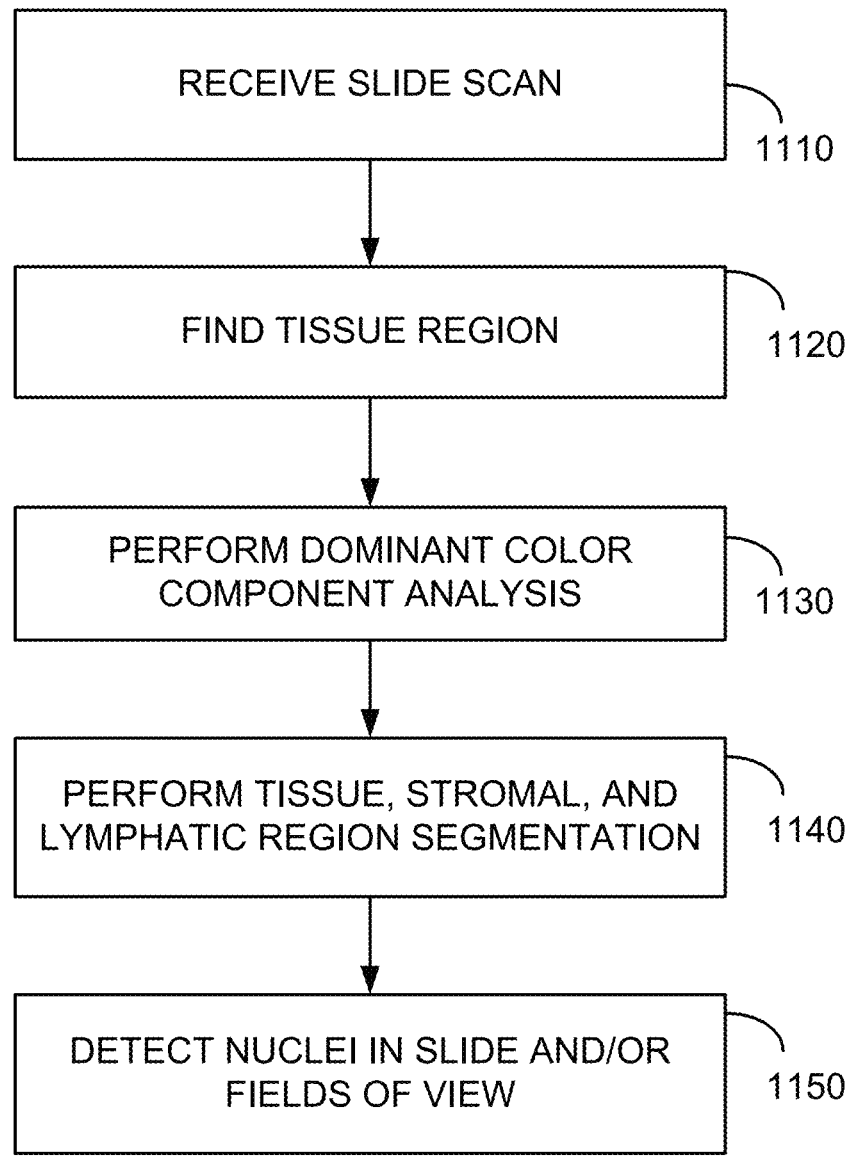
FIG. 11 is a flowchart of an exemplary computer-implemented method for identifying nuclei in a slide.

Exemplary Determination of Percent Positivity Implementation: Nuclei Identification FIG. 11 is a flowchart of an exemplary computer-implemented method 1100 for identifying nuclei in a slide. In the example, the method 1100 can use information on the slide outside of the fields of view for the analysis.

At 1110, a slide scan of a breast tissue section stained as described herein is received. Such a scan can be performed at a first magnification (e.g., 20×, 40×, or the like) and/or resolution.

At 1120, the tissue region of the slide is identified. The slide scan can be separated into glass background and tissue region. Such analysis can be performed at a second magnification (e.g., 1×, 2×, or the like) and/or resolution.

At 1130, a dominant color component analysis may be performed on the tissue region. For example, dominant colors can be extracted from the tissue region in the slide. Such analysis can be performed at a third magnification (e.g., 5× or the like) and/or resolution.

At 1140, segmentation may be performed to segment the tissue region into different labeled regions using color and texture features from multiple magnifications.

At 1150, the nuclei in the slide and/or fields of view are detected and counted (e.g., according to whether they are positive or negative stained). Scoring can thus be achieved.

Other techniques for identifying nuclei can be used. For example, any technique using color differentiation (e.g., between positive brown and negative blue) and shape (e.g., morphological analysis) of candidate nuclei can be used to identify nuclei. In such techniques, morphological post-processing can filter out stromal cells and stray blobs.

Exemplary Determination of Percent Positivity Implementation: FOV Scoring

Figure 12:
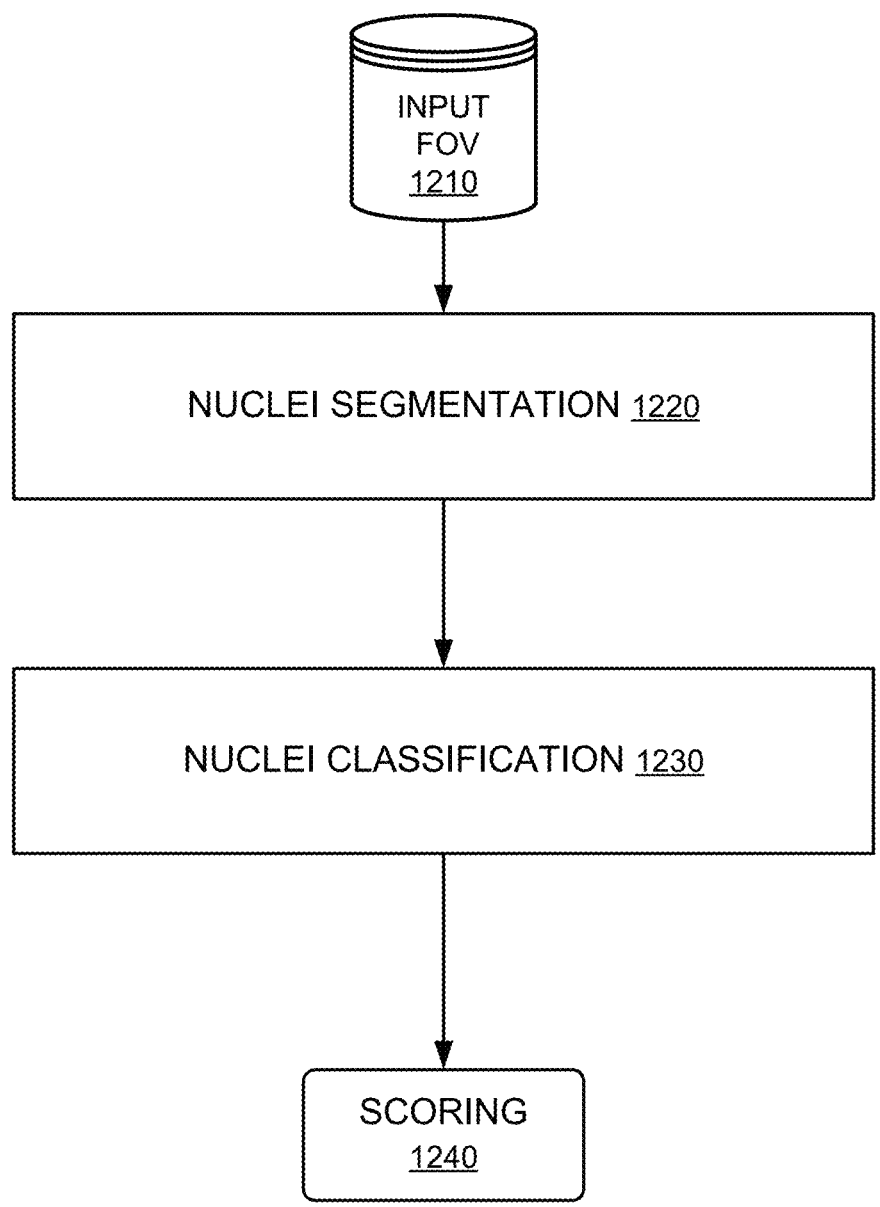
FIG. 12 is a block diagram of an exemplary system for field-of-view scoring.

FIG. 12 is a block diagram of an exemplary system 1200 for field-of-view scoring. In the example, an input field-of-view 1210 is shown. However, such analysis can be performed for multiple fields of view, one or more tiles of the slide, the entire slide, or any other input image.

Nuclei segmentation (e.g., identification of nuclei in an image) 1220 can be performed to identify nuclei in the FOV. Any number of techniques can be used to identify the nuclei.

Nuclei classification 1230 can then be performed to classify the identified nuclei. Again, any number of techniques can be used to so classify the nuclei as positive or negative stained.

At 1240, scoring is performed on the classified nuclei, resulting in percent positivity for the biomarker. By identifying nuclei, corresponding cells are identified. Scoring can be performed for a particular field of view, even if the analysis is performed on areas outside of the field of view.

Exemplary Determination of Percent Positivity Implementation: FOV Scoring

Figure 13:
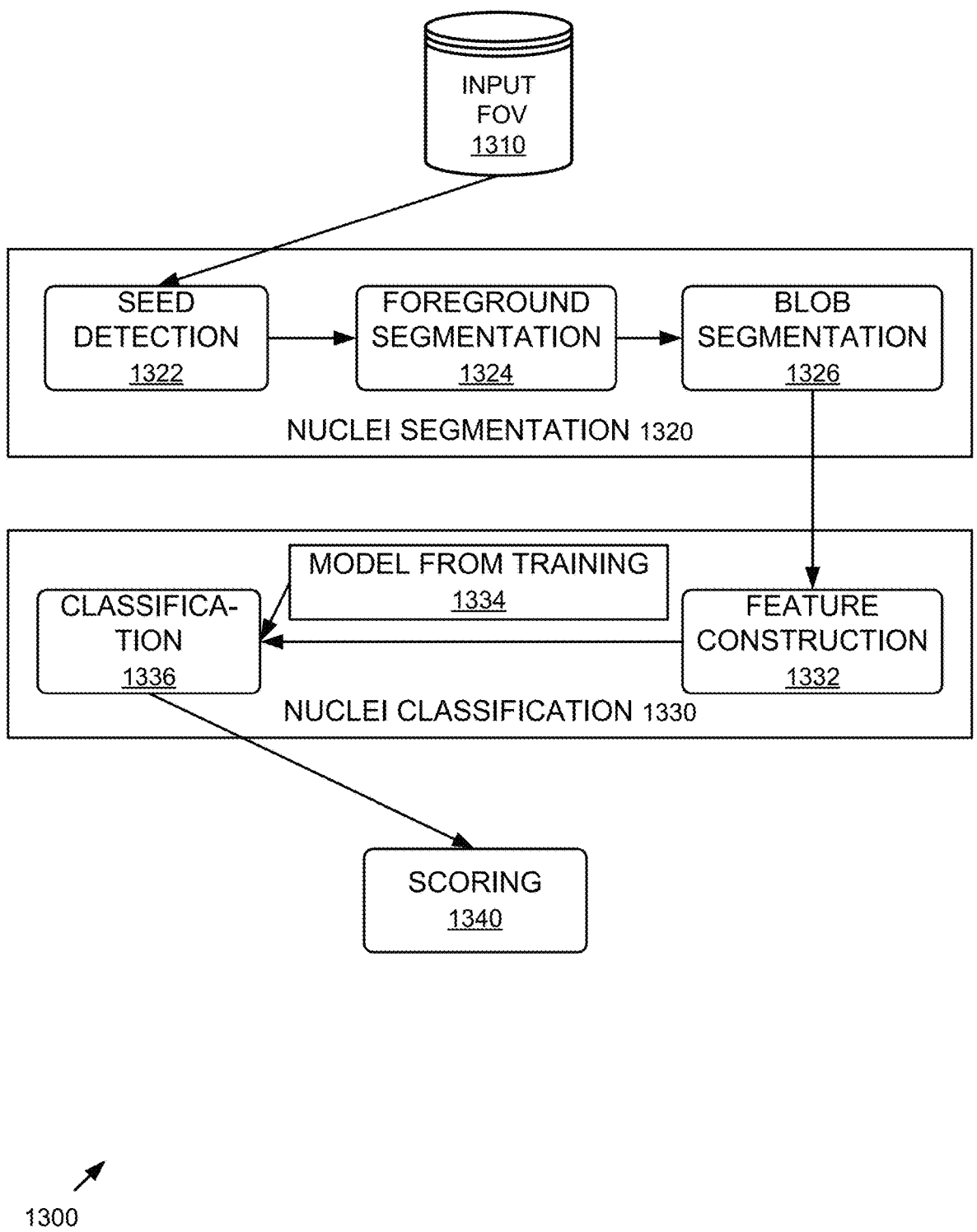
FIG. 13 is a block diagram of another exemplary system for field-of-view scoring.

FIG. 13 is a block diagram of another exemplary system 1300 for field-of-view scoring. In the example, an input field-of-view 1310 is shown. However, such analysis can be performed for multiple fields of view, one or more tiles of the slide, the entire slide, or any other input image.

Nuclei segmentation (e.g., identification of nuclei in an image) 1320 can be performed. At 1322, seed detection for the input image is performed to locate seeds processed by the system. A seed is a point that lies within a candidate nucleus and serves as a starting point for localizing cell nuclei. Seed detection can use techniques such as operating on a gradient image using a kernel based voting procedure. Foreground segmentation is performed at 1324. A foreground mask associated with nuclei regions can be computed. Blob segmentation is performed at 1326. Foreground segmentation and blob segmentation can make use of global intensity variations from image to image. A blob-like representation for each nucleus can be extracted.

Nuclei classification 1330 can be performed. At 1332, feature construction is performed. At 1336, classification is performed, with reference to a model 1334 from training Such a model can be specific to the biomarker involved.

At 1340, scoring is performed, resulting in a percent positivity for the biomarker. By identifying nuclei, corresponding cells are identified. Scoring can be performed for a particular field of view, even if the analysis is performed on areas outside of the field of view.

Exemplary Determination of Percent Positivity Implementation: Classification

Figure 14:
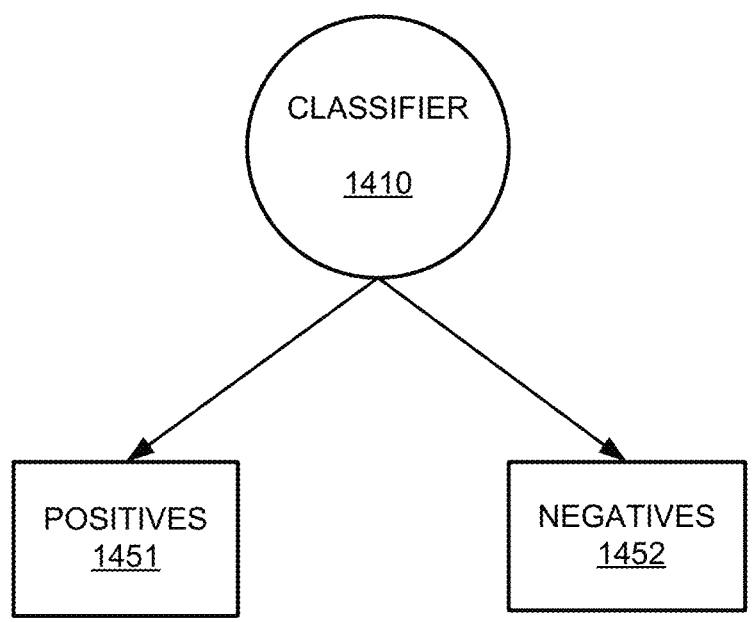
FIG. 14 is a block diagram of an exemplary classifier for determining true positive stained nuclei.

FIG. 14 is a block diagram of an exemplary classifier 1400 for determining true positive stained nuclei. In the example, candidate nuclei (e.g., incoming candidates) are processed by a classifier 1410, which separates into two classes: positives 1451 and negatives 1452. It is possible that some incoming candidates do not classify as either, are filtered out in advance, or the like. The classifier can determine negatives 1452 to be those cells (e.g., associated with nuclei) that are determined to be cells that are not stained. Some candidates (e.g., stromal tissue, lymphocytes, etc.) can be non-cells that are not included in (e.g., filtered out of) the negatives 1452 classification or the positives 1451 classification.

The classifier can use features such as color features (e.g., mean, variance, and the like), tissue background color and context, shape (e.g., size, eccentricity, elongation), morphology, cell density, and the like.

Exemplary Determination of Percent Positivity Implementation: Classification

Figure 15:
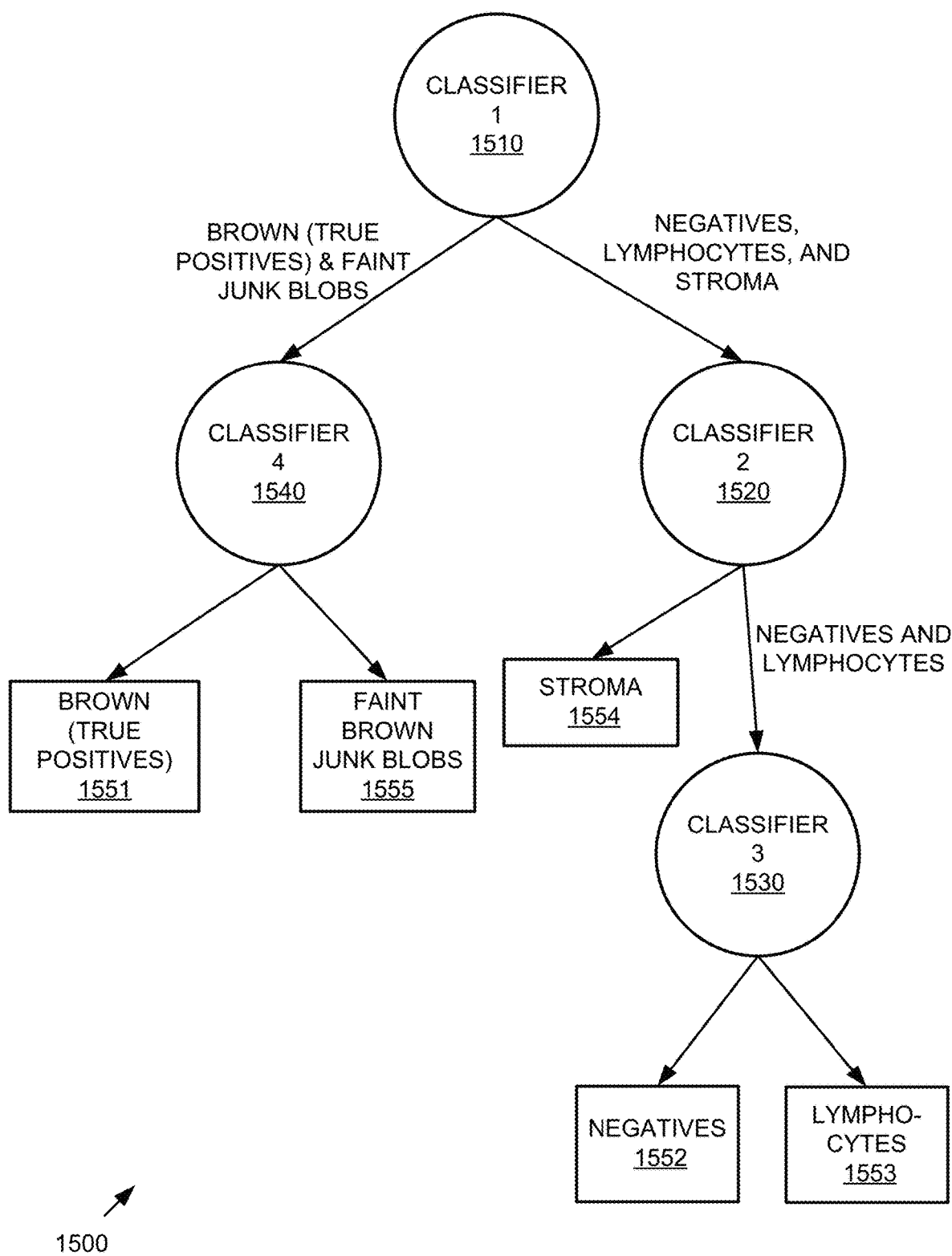
FIG. 15 is a block diagram of an exemplary multi-stage classifier for determining true positive stained nuclei.

FIG. 15 is a block diagram of an exemplary multi-stage linear binary classifier 1500 for determining true positive stained nuclei. In the example, candidate nuclei (e.g., incoming blobs) are processed by a classifier 1510, which separates into two preliminary classes:

1) brown (true positives) and faint junk blobs; and
2) negatives (e.g., unstained nuclei), lymphocytes, and stroma.

A classifier 1520 separates incoming candidates into stroma 1554 and negatives and lymphocytes.

Another classifier 1530 separates incoming candidates into negatives 1552 and lymphocytes 1553.

Still another classifier 1540 separates incoming candidates into brown (true positives) 1551 and faint brown junk blobs 1555.

The count of true positives 1551 and negatives 1552 can be used for determining percent positivity for a field of view.

The classifiers can use features such as color features (e.g., mean, variance, and the like), tissue background color and context, blob shape (e.g., size, eccentricity, elongation), morphology, cell density, and the like.

Exemplary Determination of Binned HER2 Score

In any of the examples herein, a binned score can be generated for the HER2 biomarker. For an IHC combination score, the fields of view for HER2 can be considered collectively (e.g., analysis can be performed on the digital fields of view collectively). For heterogeneity scores, a binned score can be generated for respective fields of view within an image of a tissue slide for the HER2 biomarker. In practice, such a score determines the completeness of staining for the cell membrane surrounding a nucleus.

A binned score can comprise a single number (e.g., 0, 1, 2, or 3) for HER2 (e.g., either for the FOVs collectively or respective FOVs) determined as described herein.

Exemplary Binned HER2 Score Method

Figure 16:
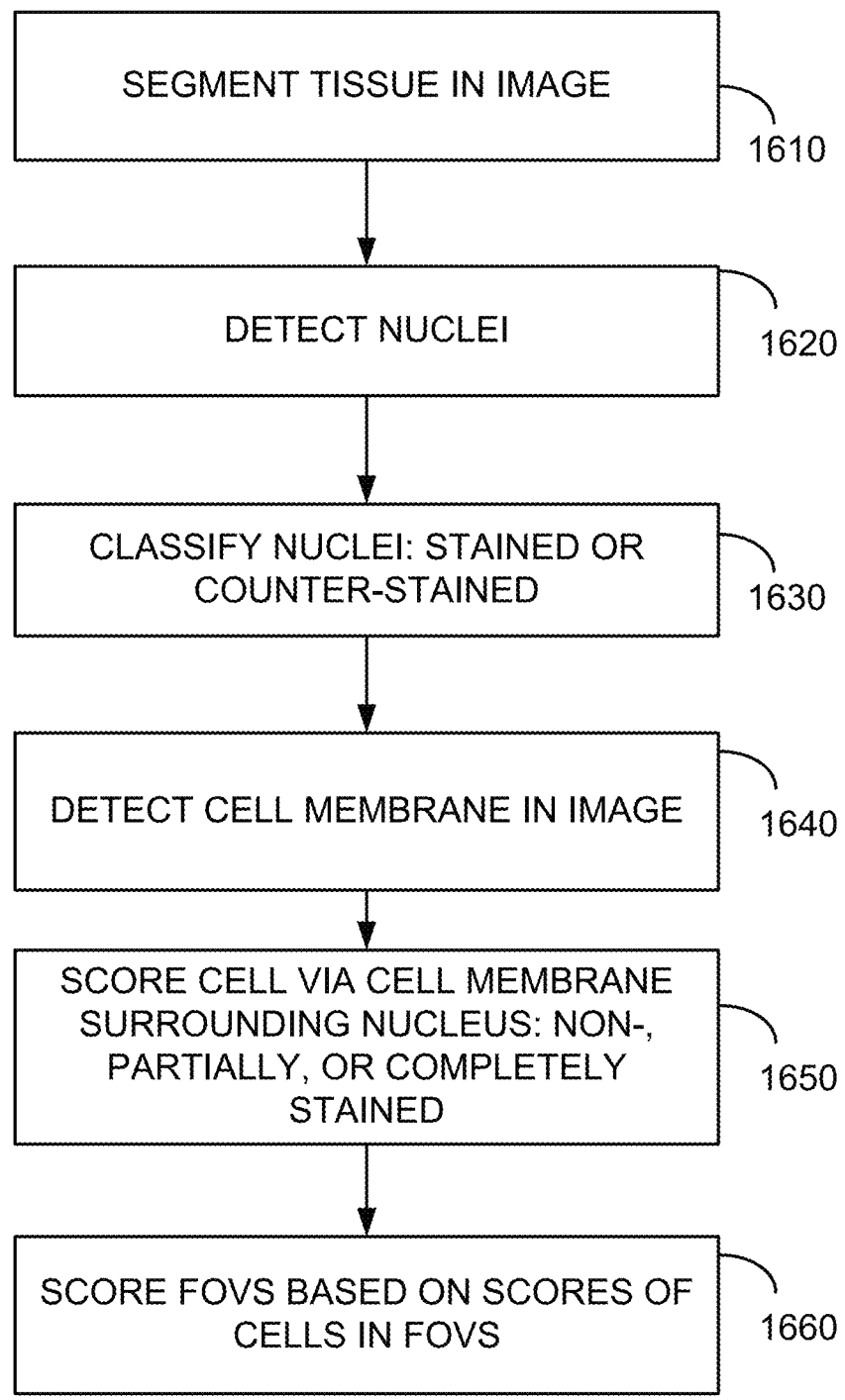
FIG. 16 is a flowchart of an exemplary method of determining a binned HER2 score.

FIG. 16 is a flowchart of an exemplary method 1600 of determining a binned HER2 score and can be used in any of the examples herein in which a binned HER2 score is used. Such a score can be generated collectively for fields of view or for separate fields of view as described herein.

The method 1600 can be performed for a given image of a slide prepared and annotated as described herein for HER2. At 1610, tissue in the image is segmented. For example, stromal and non-stromal areas can be determined.

At 1620, the nuclei can be detected as described herein, in, for example, the non-stromal (e.g., gland) regions.

At 1630, nuclei are classified as stained or counter stained.

At 1640, the stained cell membrane in the image (e.g., whole image, FOVs, or the like) is detected.

At 1650, cells are scored by associating respective nuclei with the stained membrane around them. Based on presence of stained membrane surrounding the nuclei, a cell is classified into one of the following types: non-stained (e.g., no stained membrane found around the nucleus), partially stained (e.g., the nuclei of the cell is partially surrounded by the stained membrane), completely stained (e.g., the nucleus is completely surrounded by the stained membrane). Parameters can be used as thresholds for determining partial and completely stained. If desired, such parameters can be adjusted by a user (e.g., a percentage surrounding required to qualify as partial, a percentage surrounding required to qualify as complete). For example, cells with more than a threshold amount of (e.g., 90%) surrounding stained membrane can be determined to be "completely" stained.

In practice, for the detected cells (e.g., corresponding to detected nuclei), a cell can be assigned a staining completeness indicator (e.g., indicating whether staining is complete or not, the degree of completeness, or the like) and a staining intensity value based on pixel intensity for the stain (e.g., brown) color component (e.g., ranging from 0 to a maximum value, such as 100, 255, or the like). Such information can then be analyzed to determine the HER2 score as described herein.

Thus, for a plurality of cells appearing in the digital fields of view for HER2, respective staining completeness indicators and staining intensity values can be determined. The staining completeness indicators and staining intensity values can then be analyzed via the conditions as described herein.

For a plurality of nuclei appearing in the digital fields of view for HER2, the intensity of staining of cell membrane surrounding respective of the nuclei can be determined.

At 1660, the fields of view (e.g., collectively or respectively) are scored based on scores of cells in the field of view. For example, the following conditions can be used (e.g., if the field of view qualifies for a higher score, processing need not be done for the lower scores):

| Condition | Assign Score |
|---|---|
| Responsive to determining percentage of completely stained cells > a threshold (e.g., 30%) | 3+ |
| Responsive to determining (The percentage of completely stained cells > a threshold (e.g., 10%)) OR (percentage of completely stained cells is > 0% AND membrane median intensity is less than strong intensity threshold) | 2+ |
| Responsive to determining (percentage of partially stained cells > 0%) OR (percentage of completely stained cells > 0% AND percentage of completely stained cells < a threshold (e.g., 10%) AND membrane median intensity >= strong intensity threshold AND membrane median intensity < weak intensity threshold) | 1+ |
| Responsive to determining the above conditions are not met (e.g., otherwise) | 0 |

As described, membrane median intensity can be compared with a strong intensity threshold. It can also be determined, for a plurality of nuclei appearing in digital fields of view for HER2, whether cell membrane surrounding the nuclei are completely stained.

The field of view binned scoring for HER2 can thus be achieved. If a binary score is desired, the intermediate step of determining binned score can be omitted or combined into the process.

Exemplary Staining Intensity

In any of the examples herein, positive staining (e.g., of cell membrane) can be quantified by an average brownness. For example, an average brownness on the membrane can be determined by the luminance scalar value (e.g., 0-255), which can be computed from the RGB pixel values of the membrane region. RGB values can be converted to luminance value (L) via an RGB to L*a*b* conversion technique. The L value can be converted from a 0 to 100 scale to a 0 to 255 scale.

An average brownness for a cell can be calculated by averaging L over the membrane pixels. The average brownness can be used as the median intensity (e.g., of cell membrane) as described above.

Exemplary Nuclei Classification

In any of the examples herein, nuclei can be classified for purposes of calculating the binned HER2 score. For example, cells can be classified as stained and counter stained, based on saturation, intensity, and red and blue color information in each cell from the image. Saturation and intensity information can be used to distinguish dark gray cells so they can be classified as stained instead of non-stained.

For example, the following rules can be used:

A. StainPercentage1=100*(R−G)/(R+1)

B. StainPercentage2=100*(R−B)/(R+1)

C. If StainPercentage1>PixellevelStain % and StainPercentage2>PixellevelStain %, then Pixel=Stained D. If Saturation<45 and Intensity<128, then Pixel=Stained E. If Saturation<128 and Intensity<55, then Pixel=Stained F. If Saturation<255 and Intensity<=30, then Pixel=Stained G. If Intensity<=20, then Pixel=Stained Using the pixel classification information, each nuclei can be classified as stained or non-stained based on the percentage of the stained pixels within each nucleus. For example, the following rules can be used:

A. If the cell level threshold>% of the stained pixels within each nuclei, then classify the cell as stained B. Else, classify it as non-stained The nuclei objects can then be filtered based on size.

Exemplary Binned HER2 Score Controls

Four cell line controls can be used to determine whether binned HER2 scores are being determined as described herein. When processed and stained as described herein, the cell lines should stain as described in the following table. The cell lines are available from Ventana Medical Systems, Inc. as catalog #781-2991.

| HER2 IHC Score | Cell Line | HER2 Gene Copy # |
|---|---|---|
| 0 | MCF-7 | 1.7 |
| 1+ | T47D | 2.9 |
| 2+ | MDA-MB-453 | 5.2 |
| 3+ | BT-474 | 18.9 |

The HER2 Gene Copy # was determined as an average of three lots of PATHWAY HER-2 4 in 1 control slides determined using PathVysion® HER2 Probe.

Additional information about HER2 scoring can be found in documentation for "PATHWAY® anti-HER-2/neu (4B5) Rabbit Monoclonal Primary Antibody" Catalog Number 790-2991 available from Ventana Medical Systems, Inc., which is hereby incorporated by reference herein.

Exemplary H-Score Calculation

In any of the examples herein, an H-score can be calculated from a field of view or fields of view collectively via automated techniques. For example, nuclei can be identified, and then cells (e.g., corresponding to the nuclei) can be categorized (e.g., binned) into four bins: 0, 1 (weakly stained), 2 (moderately stained), or 3 (strongly stained). Such a technique can be achieved by determining the average brownness of a cell or clump of cells (e.g., blob).

By examining color components (e.g., RGB or the like), the average brownness can be compared against thresholds to determine whether a cell is not stained (0), staining weakly (1+), staining moderately (2+), or staining strongly (3+). The counts of the cells in the bins can be maintained, and at the conclusion of the counting, an H-score can be calculated based on the percentage of cells in each bin as described herein.

For example, given the counts of cells in a plurality of bins associated with respective staining intensities (e.g., including a bin for zero intensity), the H-score can be calculated by summing, for the bins, the product of the percentage (e.g., percentage of cell count, such as the number of cells in a bin divided by the total number of cells) of cells in a bin by the respective intensity level associated with the bin. In an arrangement that has four bins, 0-3, the H-score will range from 0-300. The maximum score in such an arrangement is achieved if all (100%) of the cells are of intensity 3 (e.g., 0×0+0×1+0×2+100×3=300). Thus, the percentage can be treated as a whole number rather than a fraction (e.g., 50%=50). The intensity level associated with a bin can be the numerical portion of an intensity designator (e.g., 2+ is treated as 2).

Exemplary Breast Cancer Recurrence Prognosis Score

In any of the examples herein, a breast cancer recurrence prognosis score can be generated based on an IHC combination score and heterogeneity scores for one or more biomarkers. Such a prognosis score is sometimes simply called an "output prognosis score."

The score can be generated by combining the IHC combination scores and heterogeneity scores. For example, the heterogeneity scores can be added, multiplied, or otherwise combined and then operations (e.g., square root, exponent, coefficients, etc.) applied to form a heterogeneity component to the score.

The immunohistochemistry combination score can likewise be adjusted (e.g., square root, exponent, coefficients, etc.) to form an immunohistochemistry combination component to the score.

The two components can then be combined (e.g., added, multiplied, or the like).

One particular technique for calculating the output prognosis score follows:

$$F_{IHC}*IHC4+F_{Het}*\sqrt{Het_{ER}+Het_{Pr}}$$

where $F_{IHC}$ is an immunohistochemistry combination coefficient, $F_{Het}$ is a heterogeneity coefficient, and $Het_{ER}$ is a heterogeneity score for ER and $Hetp_R$ is a heterogeneity score for PR. In one implementation, $F_{IHC}$=0.03114 and $F_{HET}$=1.95119. However, the technologies can support adjustment of the coefficients as desired. For example, statistical analysis can indicate appropriate coefficients that can change in light of accumulated data (e.g., to divide patients into categories as described herein).

Exemplary Indication of Prognosis

In any of the examples herein, an indication of prognosis can comprise an output prognosis score itself, a category (e.g., red, yellow, green) based on thresholds, or the like. The indication can be of a form that indicates whether or not (or how likely) cancer is predicted to recur, based on the inputs.

The indication of breast cancer recurrence can be chosen (e.g., from a plurality of categories) based on one or more stored thresholds for the breast cancer recurrence prognosis score. For example, if the score meets a threshold, a first indication can be chosen (e.g., recurrence prognosis); if the score does not meet the threshold, a second indication can be chosen (e.g., non-recurrence prognosis).

Such categories can comprise a time component as well (e.g., expected to recur within 5 years) or the like.

Multiple indications can be supported (e.g., one category for whether cancer is expected to recur within 1 year, another category for whether cancer is expected to recur within 5 years, and the like).

Exemplary Implementation in Imaging Platform

Although the technologies can be implemented on a standalone basis, the technologies described herein can be implemented in a multi-function digital pathology platform that aids users in analysis of slide image data. For example, the technologies can be integrated into the Virtuoso image management software of Ventana Medical Systems, Inc., or comparable solutions.

Such a platform can serve as a front end for the technologies. Slide images and information collected about them (e.g., fields of view) via the digital pathology platform can be used as inputs to the technologies described herein.

Such a platform can allow pathologists the flexibility to work on cases, specimens, and images in any desired order. Slide images can be annotated, and a variety of other functionality can be made available.

The platform can be implemented in a thin-client (e.g., software as a service, cloud computing, or the like) scenario as desired.

Exemplary System with Heterogeneity Tool Implementing the Technologies

Figure 17:
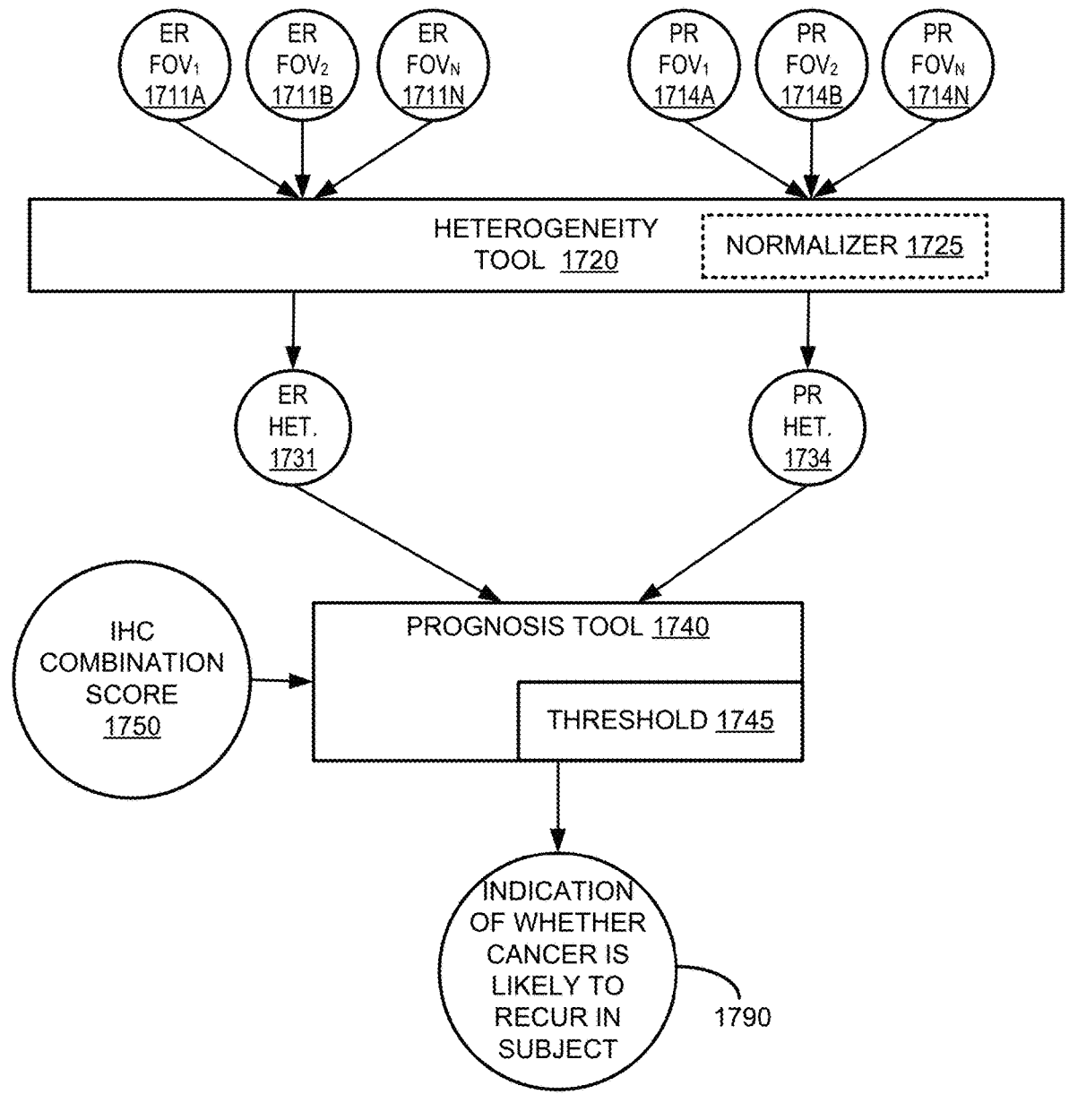
FIG. 17 is a block diagram of an exemplary system including a heterogeneity tool implementing the breast cancer prognosis technologies described herein.

FIG. 17 is a block diagram of an exemplary system 1700 including a heterogeneity tool 1720 implementing the breast cancer prognosis technologies described herein. In the example, a heterogeneity tool 1720 accepts a plurality of digital fields of view 1711A-N, 1714A-N for respective biomarkers as input and, with the assistance of an optional normalizer 1725, outputs heterogeneity scores 1731, 1734 for respective of the biomarkers.

The features of FIG. 9 can be intermingled or incorporated as desired.

A prognosis tool 1740 accepts the heterogeneity scores 1731, 1734 and IHC combination score 1750 as input and, with reference to a prognosis threshold 1745, outputs an indication 1790 of whether cancer is likely to recur in the subject.

Figure 18:
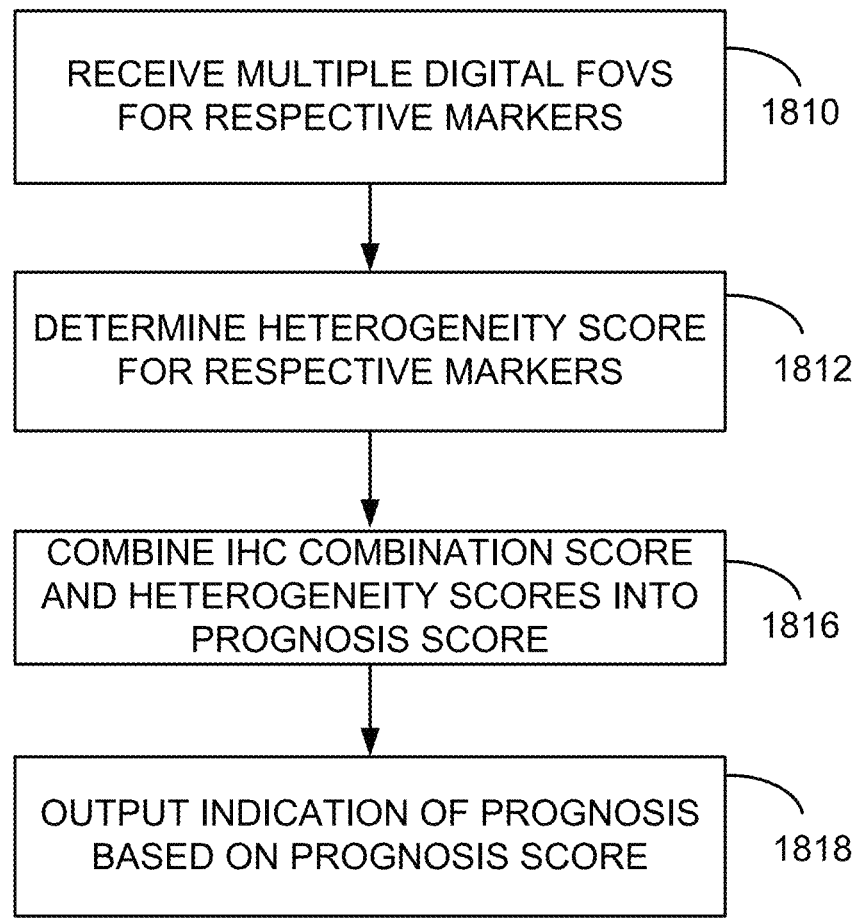
FIG. 18 is a flowchart of an exemplary computer-implemented method implementing the breast cancer prognosis technologies described herein via determining a heterogeneity score for respective biomarkers.

Exemplary Computer-Implemented Method Implementing the Technologies Via Heterogeneity Score for Respective Biomarkers FIG. 18 is a flowchart of an exemplary computer-implemented method 1800 implementing the breast cancer prognosis technologies described herein via determining a heterogeneity score for respective biomarkers and can be implemented, for example, in the system shown in FIG. 17.

At 1810, a plurality of digital fields of view are received for respective biomarkers.

At 1812, based on the digital fields of view, a heterogeneity score for respective of the biomarkers is determined.

At 1816, an IHC combination score and the heterogeneity scores are combined into a prognosis score.

At 1818, an indication of the prognosis (e.g., an indication 1790 of whether cancer is likely to recur in the subject) is output based on the prognosis score.

Exemplary IHC Combination Score Calculation

A computer-implemented method can calculate an immunohistochemistry combination score for a subject by receiving respective pluralities of digital fields of view within respective images depicting a breast cancer sample detectably labeled with respective biomarker antibodies (e.g., for a plurality of biomarkers as described herein).

Then, the percent positivity for a plurality of the biomarkers can be determined as described herein.

Then, the immunohistochemistry combination score can be calculated. Such calculation can comprise combining the percent positivity for one biomarker with the percent positivity for a second biomarker.

An immunohistochemistry combination score can then be output.

The biomarkers can comprise HER2, and calculating the IHC combination score can comprise calculating a HER2 score (e.g., binned, binary, or the like) as described herein.

Exemplary Biomarkers

In the example of FIG. 17, the biomarkers ER and PR are used for determining regional heterogeneity. In practice, the heterogeneity of different combinations of biomarkers can be calculated and combined with an IHC combination score to generate a prognosis score.

Biomarkers that can be used can include combinations of one or more of the biomarkers used as part of the IHC combination score (e.g., ER, PR, Ki-67 and HER2). Any of the other examples herein can be modified accordingly (e.g., to obtain fields of view, calculate heterogeneity scores, or the like).

Exemplary Multiplexing

In any of the examples herein, biomarkers can be measured in a multiplex scenario. For example, as described herein, a single tissue section can be labeled with more than one antibody (such as two antibodies specific for two different biomarkers, etc.), as long as such labeled proteins are distinguishable, for example by using differently labeled-secondary antibodies.

Exemplary Tissue Microarray Techniques

In any of the examples herein, tissue microarray techniques can be applied to accomplish tissue staining. For example, a plurality of tissue samples can be applied to a single substrate, and a plurality of staining agents (e.g., labeling antibodies) can be applied to the samples (e.g., a different agent per tissue sample). The techniques described herein can then be used to determine one or more scores as described herein (e.g., based on images of the detectably labeled tissue samples).

Exemplary Thresholds

In any of the examples herein, thresholds can be derived by statistical evaluation. For example cut-points can be determined using training and testing to validate an optimal cut-point that best defines high versus low risk patients.

Exemplary System with Difference Engine Implementing the Technologies

Figure 19:
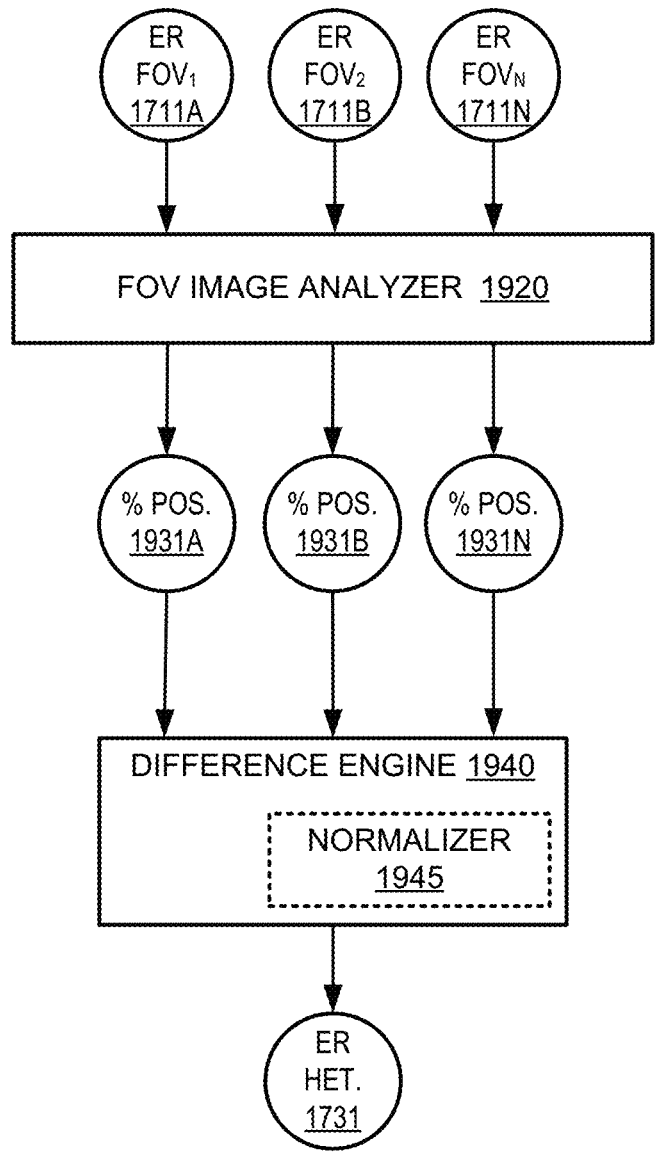
FIG. 19 is a block diagram of an exemplary system including a difference engine for calculating a heterogeneity score for a biomarker.

FIG. 19 is a block diagram of an exemplary system 1900 including a difference engine 1940 for calculating a heterogeneity score for a biomarker. The features of FIG. 9 and/or FIG. 17 can be incorporated or intermingled as desired.

In the example, a field of view image analyzer 1920 accepts digital fields of view 1711A-N (e.g., for a single biomarker) as input and outputs percent positivity measurements 1931A-N for respective of the fields of view.

The difference engine 1940 accepts the percent positivity measurements 1931A-N as input and, with assistance of an optional normalizer 1945, outputs a heterogeneity score 1731 for the biomarker.

Exemplary Computer-Implemented Method for Calculating Heterogeneity Score

Figure 20:
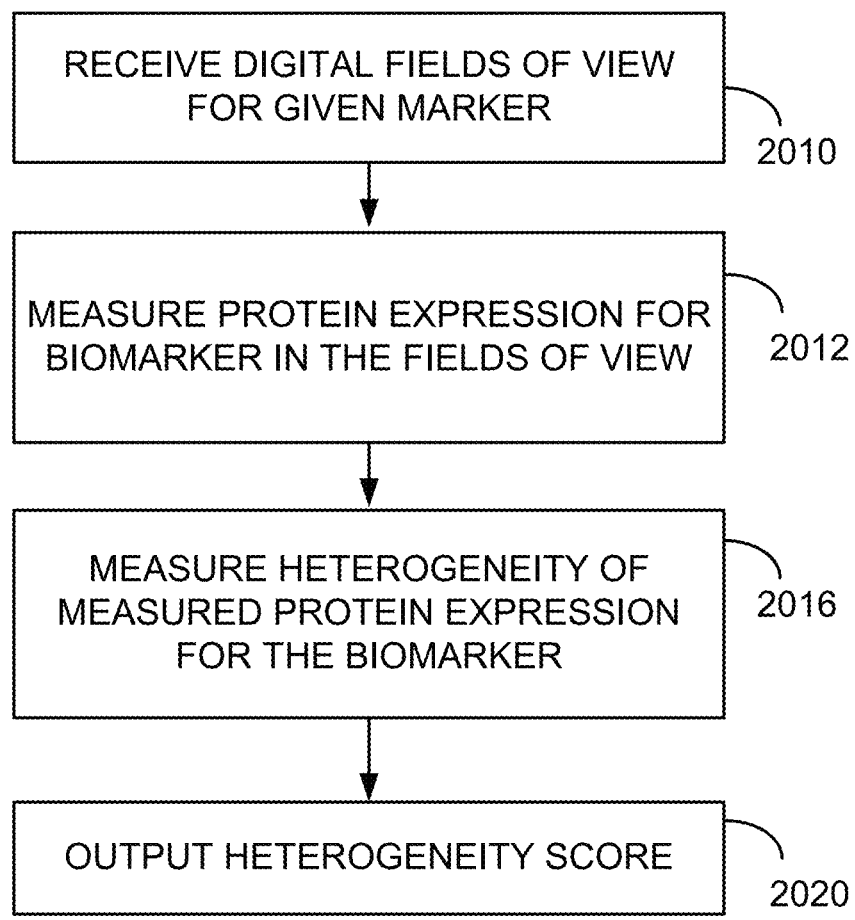
FIG. 20 is a flowchart of an exemplary computer-implemented method for calculating a heterogeneity score for use in the breast cancer prognosis technologies described herein.

FIG. 20 is a flowchart of an exemplary computer-implemented method 2000 for calculating a heterogeneity score for use in the breast cancer prognosis technologies described herein and can be implemented, for example, in the system shown in FIG. 19.

At 2010, a plurality of digital fields of view for a given biomarker are received. Such an image can depict a breast cancer sample from a subject detectably labeled with antibodies for a biomarker as described herein.

At 2012, protein expression for the biomarker in the digital fields of view is measured. For example, percent positivity measurements for respective of the biomarkers are received or determined.

At 2016, heterogeneity of the measured protein expression for the biomarker is measured among the plurality of digital fields of view. For example, a heterogeneity score is calculated as the variability between the percent positivity measurements appearing in the different fields of view (e.g., for a single biomarker).

The heterogeneity score (e.g., preliminary heterogeneity score or variability metric) can be normalized as described herein to adjust the heterogeneity score.

At 2020, the heterogeneity score is output for the biomarker (e.g., for use in the technologies described herein).

Exemplary User Interface

Figure 21:
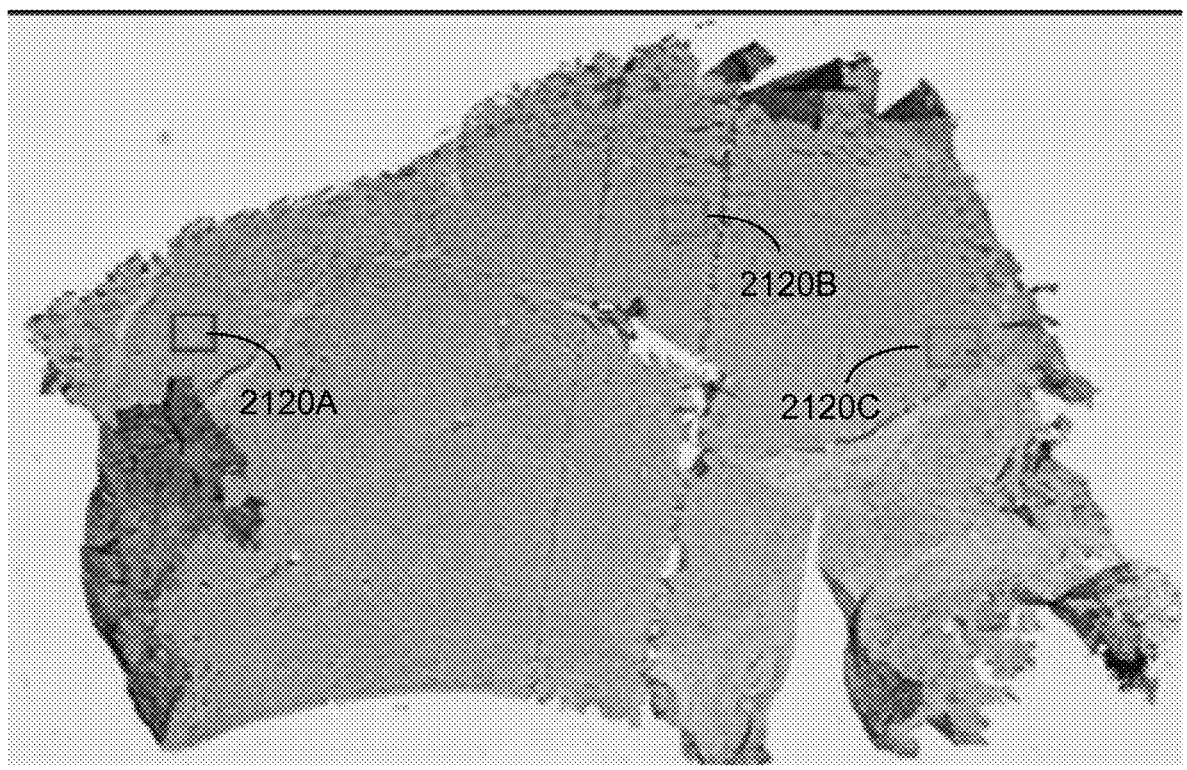
FIG. 21 is a screenshot of an exemplary user interface for indicating digital fields of view within an image.

FIG. 21 is a screenshot of an exemplary user interface 2100 for indicating digital fields of view within an image. A user interface can take the form of a window, screen, pane, or the like presented to a user for accepting input (e.g., indications of fields of view on a displayed slide image).

In the example, a pathologist has selected three fields of view 2120A, 2120B, and 2120C on a displayed slide for a particular biomarker (e.g., ER) for heterogeneity purposes. Independent fields of view can be selected for different biomarkers. Further independent fields of view can be selected for heterogeneity purposes and immunohistochemistry combination score purposes.

Exemplary Pathologist Workflow

Figure 22:
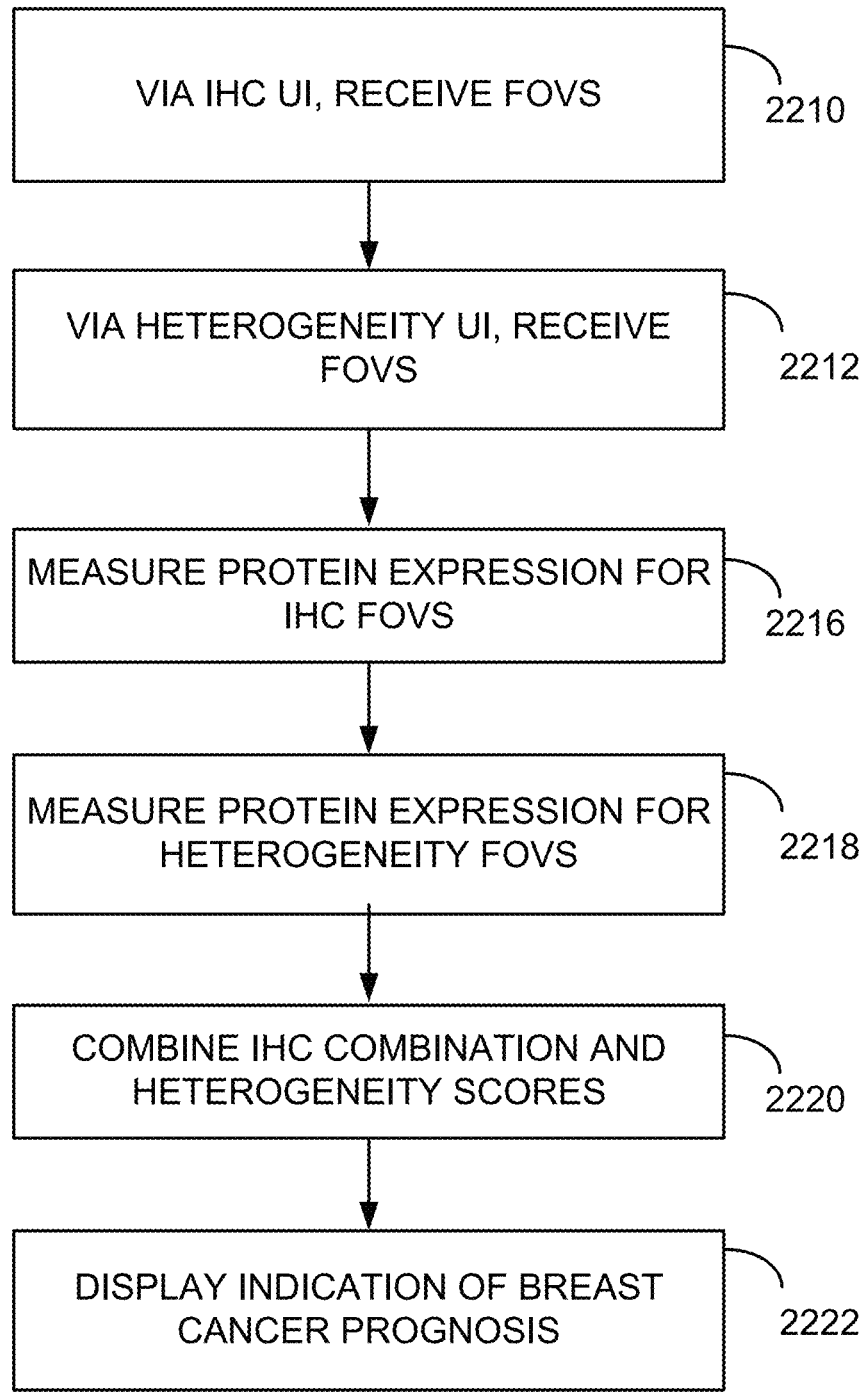
FIG. 22 is a flowchart of an exemplary digital pathologist workflow method.

FIG. 22 is a flowchart of an exemplary digital pathologist workflow computer-implemented method 2200. A digital pathologist workflow can be supported to facilitate field of view selection on (e.g., within) images.

At 2210, via a user interface requesting fields of view for an IHC combination score, a plurality of fields of view for the IHC combination score are received within a plurality of slide (or tissue) images displayed for determining the IHC combination score. Such a user interface can comprise a plurality of slide (or tissue) images depicting a breast cancer sample from a subject detectably labeled with antibodies for each of ER, HER2, Ki-67, and PR. Receiving the plurality of fields of view for the IHC combination score can comprise receiving a plurality of fields of view for each of ER, HER2, Ki-67, and PR. For example, a series of slides (or tissue sections) can be presented, and the pathologist can indicate a plurality of fields on the respective slides (e.g., FOVs for a first slide, FOVs for a second slide, etc.) (or a plurality of fields for each tissue section). Such an indication can be accomplished by receiving annotations (e.g., drawn areas) on a displayed image.

At 2212, via a user interface requesting fields of view for a heterogeneity score, a plurality of fields of view for a heterogeneity score are received within a plurality of slide (or tissue) images displayed for determining the heterogeneity score. Such a user interface can comprise a plurality of slide (or tissue) images depicting a breast cancer sample from the subject detectably labeled with antibodies for each of ER and PR. Receiving the plurality of fields of view for the IHC combination score can comprise receiving a plurality of fields of view biomarkers, such as for each of ER and PR. Such receiving can be accomplished by receiving annotations (e.g., drawn or identified areas) on a displayed image.

At 2216, protein expression values for the fields of view for the IHC combination score are measured, and an IHC combination score is calculated therefrom.

At 2218, protein expression values for the fields of view for the heterogeneity score are measured, and a heterogeneity score is calculated therefrom. One or more other heterogeneity scores for respective other biomarkers can be similarly obtained.

At 2220, the IHC combination score and the one or more heterogeneity scores are combined into a breast cancer recurrence prognosis score.

At 2222, an indication of breast cancer recurrence prognosis based on the breast cancer recurrence prognosis score is displayed (e.g., for consideration by a viewing pathologist).

Exemplary Field of View Selection

In any of the examples herein, fields of view for an IHC combination score can be selected to be representative of the entire slide. A user interface presented to the pathologist can so indicate.

In any of the examples herein, fields of view for a heterogeneity score can be selected to be representative of a region on the slide (e.g., and thus chosen to emphasize differences between regions). A user interface presented to the pathologist can so indicate.

Exemplary Further Description

A. Biological Samples

Methods of obtaining a biological sample from a subject are known in the art. For example, methods of obtaining breast tissue or breast cells are routine. For example, a sample from a tumor that contains cellular material can be obtained by surgical excision of all or part of the tumor, by collecting a fine needle aspirate from the tumor, as well as other methods known in the art.

Samples may be fresh or processed post-collection. In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago: ASCP Press, 1997). Thus, the sample can be a fixed, wax-embedded breast cancer tissue sample, such as a fixed, wax-embedded early breast cancer tissue sample. In some examples, the sample is a breast tissue section stained with hematoxylin and eosin (H&E). In some examples, the sample is a breast tissue section labeled with primary antibodies specific for ER, HER2, Ki-67 and PR, which may be labeled directly or indirectly (e.g., with a labeled secondary antibody), which in some examples is further stained with H&E.

In some examples, the sample (or a fraction thereof) is present on a solid support. Solid supports bear the biological sample and permit the convenient detection of components (e.g., proteins) in the sample. Exemplary supports or substrates include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

B. Breast Cancer Biomarkers

1. Estrogen Receptor (ER) (OMIM: 133430)

The human estrogen receptor (ER or ESR) has two different forms, referred to as α (ESR1) and β (ESR2). ER a is the form found in breast cancer cells. ER a sequences are publicly available, for example from GenBank® (e.g., accession numbers NP_001116214.1, NP_001116213.1, and P03372.2 (proteins), and NM_000125.3, NM_001122741.1, and NM_178850.2 (nucleic acids)).

The estrogen receptor is a ligand-activated transcription factor composed of several domains important for hormone binding, DNA binding, and activation of transcription. Alternative splicing results in several ESR1 mRNA transcripts, which differ primarily in their 5' untranslated regions.

Antibodies for detecting ER expression are publicly available, such as from Santa Cruz Biotechnology (Santa Cruz, Calif.), Thermo Scientific Pierce Antibodies (Rockford, Ill.), GeneTex (Irvine, Calif.), ARP American Research Products, Ventana Medical Systems, Inc. (Tucson, Ariz.) or Abcam (Cambridge, Mass.), for example Cat. Nos. sc-71064, sc-73562, and sc-7207 from Santa Cruz Biotechnology, MA1-310 from Pierce Antibodies, 790-4325 (clone SP1) from Ventana, or ab2746, ab27614, or ab37438 from Abcam.

2. Human Epidermal Growth Factor Receptor 2 (HER2) (OMIM 164870)

The human HER2 gene is located on chromosome 17 (17q21-q22). HER2 sequences are publicly available, for example from GenBank® (e.g., accession numbers NP_001005862.1, P04626.1, and NP_004439.2 (proteins) and NM_001005862.1 and NM_001982.3 (nucleic acids)).

Amplification or over-expression of HER2 plays a role in the pathogenesis and progression of certain aggressive types of breast cancer and is an important biomarker and target of therapy for the disease.

Antibodies for measuring HER2 expression are publicly available, such as from Santa Cruz Biotechnology (Santa Cruz, Calif.), Thermo Scientific Pierce Antibodies (Rockford, Ill.), GeneTex (Irvine, Calif.), ARP American Research Products, Ventana Medical Systems, Inc. (Tucson, Ariz.) or Abcam (Cambridge, Mass.), for example Cat. Nos. 790-2991 (clone 4B5) from Ventana, sc-08, sc-81528, and sc-136294 from Santa Cruz Biotechnology, and ab2428, ab16901 or ab36728 from Abcam.

3. Ki-67 (OMIM: 176741)

The human Ki-67 gene is located on chromosome 10. Ki-67 sequences are publicly available, for example from GenBank® (e.g., accession numbers NP_001139438.1, P46013.2 and NP_002408.3 (proteins) and NM_001040058.1 and NM_001145966.1 (nucleic acids)).

Ki-67 is a marker that can be used to determine the growth fraction of a given cell population. The fraction of Ki-67-positive tumor cells (the Ki-67 labeling index) is often correlated with the clinical course of cancer, such as breast cancer. Thus, Ki-67 can be used to prognose patient survival and tumor recurrence.

Antibodies for measuring Ki-67 expression are publicly available, such as from Santa Cruz Biotechnology (Santa Cruz, Calif.), Thermo Scientific Pierce Antibodies (Rockford, Ill.), GeneTex (Irvine, Calif.), ARP American Research Products, Ventana Medical Systems, Inc. (Tucson, Ariz.) or Abcam (Cambridge, Mass.), for example Cat. Nos. 790-4286 (clone 30-9) from Ventana, sc-101861 (clone MIB-1), sc-15402, and sc-23900 from Santa Cruz Biotechnology, and ab15580, ab16667 or ab8191 from Abcam.

4. Progesterone Receptor (PR) (OMIM: 607311)

The human PR gene (also known as nuclear receptor subfamily 3, group C, member 3, NR3C3) is located on chromosome 11q22. PR sequences are publicly available, for example from GenBank® (e.g., accession numbers NP_000917.3, AAA60081.1, and AAS00096.1 (proteins) and NM_001202474.1 and NM_000926.4 (nucleic acids)).

Amplification or over-expression of PR has been shown in some breast cancers.

Antibodies for measuring PR expression are publicly available, such as from Santa Cruz Biotechnology (Santa Cruz, Calif.), Thermo Scientific Pierce Antibodies (Rockford, Ill.), GeneTex (Irvine, Calif.), ARP American Research Products, Ventana Medical Systems, Inc. (Tucson, Ariz.) or Abcam (Cambridge, Mass.), for example Cat. Nos. 790-2223 (clone IE2) from Ventana, sc-810, sc-811, and sc-539 from Santa Cruz Biotechnology, and ab2765, ab2764 or ab68195 from Abcam.

5. Variant Sequences

In addition to the specific ER, HER2, Ki-67 and PR publicly available sequences provided herein, one skilled in the art will appreciate that variants of such sequences may be present in a particular subject. For example, polymorphisms for a particular gene or protein may be present. In addition, a sequence may vary between different organisms. In particular examples, a variant sequence retains the biological activity of its corresponding native sequence. For example, a ER, HER2, Ki-67 or PR sequence present in a particular subject may can have conservative amino acid changes (such as, very highly conserved substitutions, highly conserved substitutions or conserved substitutions), such as 1 to 5 or 1 to 10 conservative amino acid substitutions. Exemplary conservative amino acid substitutions are shown in Table 1.

TABLE 1

Exemplary conservative amino acid substitutions

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some embodiments, an ER, HER2, Ki-67 or PR sequence is a sequence variant of a native ER, HER2, Ki-67 or PR sequence, respectively, such as a nucleic acid or protein sequence that has at least 99%, at least 98%, at least 95%, at least 92%, at least 90%, at least 85%, at least 80%, at least 75%, at least 70%, at least 65%, or at least 60% sequence identity to the sequences set forth in a GenBank® accession number referred to herein, wherein the resulting variant retains ER, HER2, Ki-67 or PR biological activity. "Sequence identity" is a phrase commonly used to describe the similarity between two amino acid sequences (or between two nucleic acid sequences). Sequence identity typically is expressed in terms of percentage identity; the higher the percentage, the more similar the two sequences.

Methods for aligning sequences for comparison and determining sequence identity are well known in the art. Various programs and alignment algorithms are described in: Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA*, 85:2444, 1988; Higgins and Sharp, *Gene*, 73:237-244, 1988; Higgins and Sharp, *CABIOS*, 5:151-153, 1989; Corpet et al., *Nucleic Acids Research*, 16:10881-10890, 1988; Huang, et al., *Computer Applications in the Biosciences*, 8:155-165, 1992; Pearson et al., *Methods in Molecular Biology*, 24:307-331, 1994; Tatiana et al., *FEMS Microbiol. Lett.*, 174:247-250, 1999. Altschul et al. present a detailed consideration of sequence-alignment methods and homology calculations (*J. Mol. Biol.*, 215:403-410, 1990).

The National Center for Biotechnology Information (NCBI) Basic Local Alignment Search Tool (BLAST™, Altschul et al., *J. Mol. Biol.*, 215:403-410, 1990) is publicly available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the Internet under the help section for BLAST™.

For comparisons of amino acid sequences of greater than about 15 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=3]; reward for a match [default=1]; expectation value (E) [default=10.0]; word size [default=3]; and number of one-line descriptions (V) [default=100]. When aligning short peptides (fewer than around 15 amino acids), the alignment should be performed using the Blast 2 sequences function "Search for short nearly exact matches" employing the PAM30 matrix set to default parameters (expect threshold=20000, word size=2, gap costs: existence=9 and extension=1) using composition-based statistics.

C. Detection of Proteins

In particular examples, a sample obtained from the subject is analyzed to determine if it contains detectable levels of ER, HER2, Ki-67 and PR protein, such as a breast cancer sample. Thus, the sample can be analyzed to detect or measure the presence of ER, HER2, Ki-67 and PR proteins in the sample, for example a qualitative or quantitative measurement. The expression patterns of ER, HER2, Ki-67 and PR proteins can also be used to determine the heterogeneity of the protein expression.

Methods of detecting proteins are routine. In some examples, immunoassays are used to detect the presence of ER, HER2, Ki-67 and PR proteins in the sample. Generally, immunoassays include the use of one or more specific binding agents (such as antibodies) that can substantially only bind to the target peptide, such as ER, HER2, Ki-67 and PR. Such binding agents can include a detectable label (such as a radiolabel, fluorophore or enzyme), that permits detection of the binding to the protein. Exemplary immunoassays that can be used include, but are not limited to: Western blotting, ELISA, fluorescence microscopy, and flow cytometry. A particular immunoassay is immunohistochemistry.

In one example, the specific binding agent is an antibody, such as a polyclonal or monoclonal antibody, or fragment thereof. In some examples, the antibody is a humanized antibody. In some examples, the antibody is a chimeric antibody. If desired, the antibody can include a detectable label to permit detection and in some cases quantification of the target protein/antibody complex. In other examples, the antibody is detected with an appropriate labeled secondary antibody.

In some examples, the antibodies for ER, PR, HER2 and Ki-67 are obtained from Ventana Medical Systems, Inc. (Tucson, Ariz.). However, one skilled in the art will appreciate that other antibodies that can be used in the methods and kits provided herein are commercially available from other sources, such as: Novus Biologicals (Littleton, Colo.), Santa Cruz biotechnology, Inc. (Santa Cruz, Calif.), Abcam (Cambridge, Mass.), and Invitrogen (Carlsbad, Calif.).

The presence of detectable signal above background or control levels indicates the presence of a target peptide (e.g., ER, HER2, Ki-67 and PR protein) in the sample. The value obtained for the test breast cancer sample can be compared to a reference value, such as a reference value representing a value or range of values expected. In some examples, the reference is a sample possessing a known or expected amount of ER, HER2, Ki-67 and PR protein.

In some examples, a breast cancer sample is obtained, and processed for IHC. For example, the sample can be fixed and embedded, for example with formalin and paraffin. The sample can then be mounted on a support, such as a glass microscope slide. For example, the sample can be microtomed into a series of thin sections, and the sections mounted onto one or more microscope slides. In some examples, a single slide includes multiple tissue sections. Different sections of the breast cancer sample can then be individually labeled with antibodies specific for ER, HER2, Ki-67 or PR protein. That is, one section can be labeled with ER-specific antibodies, and another section can be labeled with HER2-specific antibodies, and so on. In some examples, a single section of the breast cancer sample can be labeled with antibodies specific for two or more of ER, HER2, Ki-67 or PR protein. That is, one section can be labeled with ER-specific antibodies and with HER2-specific antibodies, and the antibodies distinguish by using different labels (wherein each label is specific for ER, HER2, Ki-67 or PR). For example, the BenchMark ULTRA from Ventana Medical Systems, Inc. can be used to stain and process the slides.

In some examples the slides containing the labeled sample are scanned and digitized, for example using the iScan Coreo (Ventana). Thus, for each of ER, HER2, Ki-67 and PR protein (which are detectably labeled in the sample), at least one digital image can be obtained. Subsequently, two or more fields of view (FOV) for each protein (ER, HER2, Ki-67 and PR protein) are selected and annotated, for example by a pathologist.

D. Calculating an IHC Combination Score

To calculate the IHC combination (e.g., IHC4) score, a breast cancer sample with detectably labeled ER, HER2, Ki-67 and PR (for example one or more slides, such as 1, 2, 3 or 4 slides) is used. In one example, the breast cancer sample can be labeled with primary antibodies specific for each of ER, HER2, Ki-67 and PR, and appropriately labeled secondary antibodies (such as those labeled with a fluorophore or enzyme, such as DIG). In one example, the ultraView Red ISH DIG detection Kit is used as per the manufacturer's instructions (Ventana Medical Systems, Inc., Catalog #760-505).

One or more digital images of one or more slides containing the labeled breast cancer sample can be obtained, for example using microscope image scanning software. The one or more slides containing the one or more labeled breast cancer samples (or a digital image thereof) is evaluated for its overall staining, for example by a pathologist. For example, regions of heterogeneity in the staining can be detected for each of ER, HER2, Ki-67 and PR. If regional heterogeneity is observed, at least one FOV having regional heterogeneity is selected (such as at least 2, at least 3, at least 4, or at least 5 different FOV areas of regional heterogeneity on the slide, such as 2, 3, 4, 5, 6, 7, 8, 9, or 10 FOVs), along with at least two other FOV that are similar to one another (such as at least 3, at least 4, or at least 5 different FOV areas on the slide that are similar to one another, such as 2, 3, 4, 5, 6, 7, 8, 9, or 10 FOVs). If no regional heterogeneity is observed, fewer FOV can be selected, such as at least 2, at least 3, at least 4, or at least 5 different FOV on the slide, such as 2, 3, 4 or 5 FOV on the slide.

For each FOV selected for PR and Ki-67 protein, the percent positivity is determined. Thus, if four FOV are selected for PR, then % positivity is determined for each of the four FOV. To calculate the % positivity, the total number of tumor cells in the FOV as well as the total number of tumor cells stained in the FOV (e.g., that are PR+) is determined. The % positivity is the total number of tumor cells stained in the FOV divided by the total number of tumor cells in the FOV. The % positivity for each FOV for a particular marker (e.g., PR) is averaged, resulting in a % positivity for PR and Ki-67.

For each FOV for HER2, a binned score (on a sale of 0-3) is determined. For example, for each FOV, a binned score between 0 and 3 can be assigned to the staining based on evaluation of the FOV. A four-point scale can be used to describe the immunostaining of membrane surrounding a nucleus for HER2, as follows: 0, negative; 1, weak positivity; 2, moderate positivity; and 3+, strong positivity, for example as shown in Table 2. Cytoplasmic staining may still be present, but such staining need not be included in the determination.

TABLE 2

HER2 binned scores

| Staining Pattern | Score | HER2 Staining Assessment |
|---|---|---|
| No membrane staining is observed | 0 | Negative |
| Faint, partial staining of the membrane | 1+ | Negative |
| Weak complete staining of the membrane, greater than 10% of cancer cells | 2+ | Positive |
| Intense complete staining of the membrane, greater than 10% of cancer cells | 3+ | Positive |

Alternatively, a binary score (0 or 1) can be determined for HER2 (e.g., based on individual FOVs or the FOVs collectively), wherein a positive result (1) corresponds to a staining score of 2 or 3, and a negative result (0) corresponds to a staining score of 0 or 1. Greater or less resolution can be used. For example a system using 0, 1, 2, and 3 can be used. Internally, the score for HER2 can be represented as a binned score (e.g., 0, 1, 2, or 3) or as a binary value (e.g., 0 or 1) (e.g., the binary value is determined based on the binned score).

For the FOVs selected for ER, an H-score is determined (e.g., for the individual FOVs or the FOVs collectively). The H-score for ER is the percentage of cells showing weak staining, added to two times the percentage of cells staining moderately, added to three times the percentage of cells staining intensely, that is divided by 30 to arrive at a variable between 0-10 ($ER_{10}$). An H-score of more than 1 is positive. The percentage of cells staining positive for PR (e.g., capped at 10%) was divided by 10 to obtain a variable between 0 and 10 ($PR_{10}$).

Thus, after FOVs are identified by a pathologist for each of the four markers, an imaging algorithm can extract digital information from the slide (such as a breast cancer sample labeled to detect ER, HER2, Ki-67 or PR protein), transforming the digital image into score components (e.g., measurements of % positivity, binned (or binary) score, and H-score). These scores for each marker described above are used to generate an IHC combination score, which is calculated using the formula:

IHC4=94.7×{−0.100$ER_{10}$−0.079$PR_{10}$+0.586HER2+ 0.240 ln(1+10×Ki67)}

E. Calculating a Heterogeneity Score

Heterogeneity refers to the spatial variation of histochemical and molecular staining patterns, such as the staining patterns for breast cancer biomarkers ER, HER2, Ki-67 and PR in a breast cancer sample. Heterogeneity can be an indicator of the spatial variation of tumor aggressiveness and/or growth patterns that can be correlated with an aggregated clinical phenotype (e.g., a tumor likely to recur). It is shown herein that biological heterogeneity of ER, PR, HER2 and Ki-67 protein expression is correlated with the unpredictable recurrence of a fraction of early stage breast cancer patients.

The method includes quantifying the regional heterogeneity in the sample for each of the four markers, which is computed from the scores from the selected FOV. Thus, for each marker, a quantitative measure of regional heterogeneity is determined. If the marker is homogenous or not detectable (e.g., HER2−), then that value will fall out of the heterogeneity score calculation. Two or more fields of view (FOV) for each protein (ER, HER2, Ki-67 and PR protein) are selected and annotated, for example by a pathologist. The FOV selected can be the same or different from the FOV selected to calculate the IHC4 score.

In some examples, a plurality of FOVs (e.g., at least 3, at least 4, or at least 5 FOVs, or the like) are selected, for example, 2, 3, 4, 5, 6, 7, 8, 9 or 10 FOVs. As described above, responsive to observing regional heterogeneity, more FOVs may be selected, such as at least one FOV having regional heterogeneity (such as at least 2, at least 3, at least 4, or at least 5 different FOV areas of regional heterogeneity on the slide, such as 2, 3, 4, 5, 6, 7, 8, 9, or 10 FOVs), along with at least two other FOVs that are similar to one another (such as at least 3, at least 4, or at least 5 different FOV areas on the slide that are similar to one another, such as 2, 3, 4, 5, 6, 7, 8, 9, or 10 FOVs). Responsive to observing no regional heterogeneity, fewer FOVs may be selected, such as at least 2, at least 3, at least 4, or at least 5 different FOVs on the slide, such as 2, 3, 4 or 5 FOVs on the slide.

In some cases, it may be desirable to select additional FOVs to conclusively establish (e.g., confirm or prove) that regional heterogeneity is not present. However, if it is conclusively apparent that there is no regional heterogeneity, selecting additional FOVs may unnecessarily expend resources; therefore, fewer FOVs may be selected.

In one example, FOVs with different % positivity are selected, as these areas indicate heterogeneity, for example regional heterogeneity.

For each of ER, Ki-67, HER2 and PR protein, a heterogeneity score is determined. In some examples, HER2 is not determined (or the value falls out as there is no heterogeneity for HER2), for example if the sample is HER2 negative. In some examples, Ki-67 is not determined (or the value falls out as there is no heterogeneity for Ki-67).

For the ER and PR markers (and in some examples also HER2 and Ki-67) the heterogeneity score is calculated as follows. The variability of percent positivity scores are calculated from heterogeneous regions in the selected FOV. For example, a variability metric (VM) for each marker can be determined, wherein the VM is an indication of how different one selected FOV is from another FOV for the same protein. There are many ways this can be calculated, such as determining a standard deviation. In one example, the VM for each of ER, PR, and Ki-67 (and in some examples HER2) is calculated as follows:

VM=STD($PPFS_1$,$PP(FS_2)$, ... $PP(FS_N)$)

wherein PP(FS) is the percent positivity for each field of view, FS. Percent positivity can be calculated as described herein. Then the heterogeneity score for the marker (e.g., ER and PR) is calculated using the formula (where α=[0,1]:

$$H = \begin{cases} \alpha * \dfrac{VM}{0.05}, & S < 10\% \\ \alpha * \dfrac{VM}{S}, & \text{otherwise} \end{cases},$$

For HER2, a binned score, P(FS) (0 to 3 scale, see above) is computed for each FOV, FS. HER2 heterogeneity score can then calculated using the formula:

$$H = \sum_{\substack{\forall i,j \\ i \neq j}} \|P(FS_i) - P(FS_j)\|$$

If the binned scores are the same for each FOV, the heterogeneity score for HER2 is 0.

The following table indicates different types of heterogeneity, including regional heterogeneity as described herein.

TABLE 3

Types of heterogeneity

|  | Generic | ER protein | PR protein | Ki67 protein | HER2 protein | HER2 gene |
|---|---|---|---|---|---|---|
| Geographic 2 separate blocks, >2 in apart | Diffuse - focal | Not applicable | n.a. | n.a. | n.a. | n.a |
| Regional 1 4x-FOV apart, same section/block, 0.25-2 in | Diffuse - focal | Yes | Yes | Yes | Yes | Yes |
| Inter-glandular Within 4x-FOV, <0.25 in For both regional categories | > or <50% similar formations | No | No | No | Yes | Yes |
| Intra-glandular = cell-cell | > or <50% similar cells | Yes | Yes | Yes | Yes | Yes |
| All formations in 1 20x-FOV | If multilayered, all or specific layers | No | No | No | No | No |
| For all regional and inter-glandular categories | Diffuse - polarized | No | No | No | No | No |
| Sub-cellular | Nuclear, cytoplasmic or membraeous For all regional, inter- and intra-glandular categories | Nuclear | Nuclear | Nuclear | Membranous | Nuclear |
| Intensity | Negative, 3 positive categories | Yes | Yes | Yes | Yes | Yes |

F. Calculating an Output Prognosis Score

The output prognosis score is calculated from the IHC combination score and the heterogeneity score described above. A combined heterogeneity score is generated as follows and can be adjusted to include further biomarkers:

Combined heterogeneity score=square root(ER heterogeneity score+PR heterogeneity score)

The IHC combination score and the combined heterogeneity score are entered into a statistical analysis method (e.g., Cox proportional hazards model), to maximize the combined predictive capabilities of both measures. For example the model can be used to determine the progression-free survival (PFS) as outcome, such as a 1-, 3- or 5-year PFS or otherwise separate patients into categories.

The result is a mathematical formula that generates a score to predict the risk of 5-year PFS output prognosis score=0.03114*IHC4+
1.95119*combined heterogeneity score Thus, the output prognosis score either is a high risk score (which indicates that early stage breast cancer is likely to recur, for example within 5 years, such as a local recurrence or a distant metastasis) or a low risk score (which indicates that early stage breast cancer is not likely to recur).

G. Outputting Output Value and Prognosis

Following the determination of IHC combination score, heterogeneity score, and the output prognosis score, the assay results (such as the output prognosis score), findings, prognosis, predictions and/or treatment recommendations are typically recorded and communicated to technicians, physicians and/or patients, for example. In certain embodiments, computers will be used to communicate such information to interested parties, such as, patients and/or the attending physicians. Based on the prognosis of the breast cancer, the therapy administered to a subject can be modified.

In one embodiment, a prognosis, prediction and/or treatment recommendation based on the output value is communicated to interested parties as soon as possible after the assay is completed and the prognosis is generated. The results and/or related information may be communicated to the subject by the subject's treating physician. Alternatively, the results may be communicated directly to interested parties by any means of communication, including writing, such as by providing a written report, electronic forms of communication, such as email, or telephone. Communication may be facilitated by use of a suitably programmed computer, such as in case of email communications. In certain embodiments, the communication containing results of a prognostic test and/or conclusions drawn from and/or treatment recommendations based on the test, may be generated and delivered automatically to interested parties using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system.

In certain embodiments of the methods of the disclosure, all or some of the method steps, including the assaying of samples, prognosis of breast cancer, and communicating of assay results or prognosis, may be carried out in diverse (e.g., foreign) jurisdictions.

H. Follow-Up Therapies

The disclosed methods can further include selecting subjects for treatment for breast cancer, for example if the sample is prognosed as an early stage breast cancer likely to recur. Alternatively, the disclosed methods can further include selecting subjects for no treatment (for example just monitoring), if the sample is diagnosed as an early stage breast cancer not likely to recur.

In some embodiments, the disclosed methods include one or more of the following depending on the patient's prognosis: a) prescribing a treatment regimen for the subject if the subject's determined prognosis is that the early stage breast cancer is likely to recur (such as treatment with one or more radiotherapies and/or chemotherapeutic agents, additional surgery, more frequent monitoring, or combinations thereof); b) not prescribing a treatment regimen for the subject if the subject's determined prognosis is that the early stage breast cancer is not likely to recur; c) administering a treatment (such as treatment with one or more radiotherapies and/or chemotherapeutic agents, additional surgery, or combinations thereof) to the subject if the subject's determined prognosis is that the early stage breast cancer is likely to recur; and d) not administering a treatment regimen to the subject if the subject's determined prognosis is that the early stage breast cancer is not likely to recur. In an alternative embodiment, the method can include recommending one or more of (a)-(d). Thus, the disclosed methods can further include treating a subject for breast cancer.

Exemplary Score Components

In any of the examples herein, score components can refer to measurement of gene expression (e.g., percent positivity or the like), H-score, binned score, binary score, or the like for one or more biomarkers.

As components are combined, the resulting components can represent plural biomarkers.

Exemplary Further Description

For IHC computation and heterogeneity measures, in place of manual microscopy scores, the slides can be digitized and automated image analysis algorithms can compute the percent positivity, binned score (e.g., and convert to binary score) and H-Score for the fields (FOVs) selected by the pathologist.

In each digitized slide associated with the above-mentioned four markers, the pathologist annotates specific regions to quantify the inter-region intensity and regional heterogeneity. Using the automated image analysis for each region, positive and negative stained cell counts, percent positivity, and binned score (0, 1+, 2+, 3+) are computed.

To quantify the inter-region heterogeneity, heterogeneity metrics based on these regional scores can be used. The heterogeneity score is based on the negative and positive (1+, 2+ and 3+) cell counts in the FOVs selected by the pathologist. The heterogeneity score captures the variation of scores within the selected FOVs. Using the FOVs annotated by the pathologist, the score is a normalized function of the standard deviation of the scores from different FOVs. The chosen normalization parameter is marker-dependent, reflecting the fact that in general inter-region percent positivity score have higher variability for higher overall slide positivity score.

Exemplary Computing System

Figure 23:
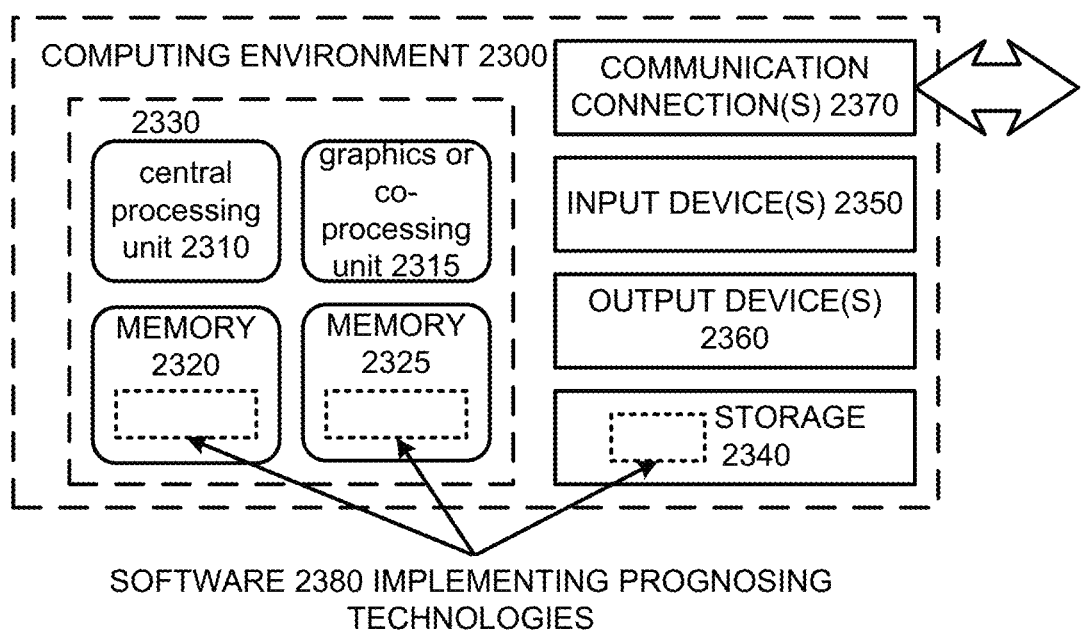
FIG. 23 is a block diagram of an exemplary computing system in which described embodiments can be implemented.

FIG. 23 illustrates a generalized example of a suitable computing system 2300 in which several of the described innovations may be implemented. The computing system 2300 is not intended to suggest any limitation as to scope of use or functionality, as the innovations may be implemented in diverse general-purpose or special-purpose computing systems. Computing systems as described herein can be used to implement automated functionality (e.g., processes, actions, and the like are performed by a computing system as described herein).

With reference to FIG. 23, the computing system 2300 includes one or more processing units 2310, 2315 and memory 2320, 2325. In FIG. 23, this basic configuration 2330 is included within a dashed line. The processing units 2310, 2315 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 23 shows a central processing unit 2310 as well as a graphics processing unit or co-processing unit 2315. The tangible memory 2320, 2325 may be volatile memory (e.g., registers, cache, RAM), non-volatile memory (e.g., ROM, EEPROM, flash memory, etc.), or some combination of the two, accessible by the processing unit(s). The memory 2320, 2325 stores software 2380 implementing one or more innovations described herein, in the form of computer-executable instructions suitable for execution by the processing unit(s).

A computing system may have additional features. For example, the computing system 2300 includes storage 2340, one or more input devices 2350, one or more output devices 2360, and one or more communication connections 2370. An interconnection mechanism (not shown) such as a bus, controller, or network interconnects the components of the computing system 2300. Typically, operating system software (not shown) provides an operating environment for other software executing in the computing system 2300, and coordinates activities of the components of the computing system 2300.

The tangible storage 2340 may be removable or non-removable, and includes magnetic disks, magnetic tapes or cassettes, CD-ROMs, DVDs, or any other medium which can be used to store information in a non-transitory way and which can be accessed within the computing system 2300. The storage 2340 stores instructions for the software 2380 implementing one or more innovations described herein.

The input device(s) 2350 may be a touch input device such as a keyboard, mouse, pen, or trackball, a voice input device, a scanning device, or another device that provides input to the computing system 2300. For video encoding, the input device(s) 2350 may be a camera, video card, TV tuner card, or similar device that accepts video input in analog or digital form, or a CD-ROM or CD-RW that reads video samples into the computing system 2300. The output device(s) 2360 may be a display, printer, speaker, CD-writer, or another device that provides output from the computing system 2300.

The communication connection(s) 2370 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-readable media. Computer-readable media are any available tangible media that can be accessed within a computing environment. By way of example, and not limitation, with the computing system 2300, computer-readable media include memory 2320, 2325, storage 2340, and combinations of any of the above.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computing device. In general, a computing system or computing device can be local or distributed, and can include any combination of special-purpose hardware and/or general-purpose hardware with software implementing the functionality described herein.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Computer-Readable Media

Any of the computer-readable media herein can be non-transitory (e.g., memory, magnetic storage, optical storage, or the like).

Any of the storing actions described herein can be implemented by storing in one or more computer-readable media (e.g., computer-readable storage media or other tangible media).

Any of the things described as stored can be stored in one or more computer-readable media (e.g., computer-readable storage media or other tangible media).

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

Methods in Computer-Readable Storage Devices

Any of the methods described herein can be implemented by computer-executable instructions stored in one or more computer-readable storage devices (e.g., memory, magnetic storage, optical storage, or the like). Such instructions can cause a computer to perform the method.

Exemplary Early Stage Breast Cancer Recurrence Risk Implementation and Results

This example describes methods used to predict early stage breast cancer recurrence risk.

Breast cancer samples from about 20 patients were labeled with antibodies specific for ER, PR, HER2, and Ki-67.

These resulting labeled samples on microscope slides were imaged using digital pathology. Three FOV were selected for each of ER, PR, HER2, and Ki-67. Software was used to quantify percent cell staining (e.g., percent positivity) and intensity for each FOV. Percent positivity was thus determined. In addition, three different measures of heterogeneity based on the variability of intensities and percent cells staining for the three FOV's were determined.

The resulting percent cell staining and intensity for each FOV for each of ER, PR, HER2, and Ki-67 were averaged (e.g., the ER FOVs were averaged). This results in a percent cell staining value and intensity value for each of ER, PR, HER2, and Ki-67. These values were used to calculate the IHC4 score using this formula:

$$IHC4 = 94.7 \times \{-0.100 ER10 - 0.079 PR10 + 0.586 HER2 + 0.240 \ln(1 + 10 \times Ki67)\}$$

Using the IHC4 score and the 12 heterogeneity values (one for each of the three FOV for each of ER, PR, HER2, and Ki-67), each of the heterogeneity measures and the IHC4 score were modeled using the cox proportional hazards model, which models time to distant recurrence. The three heterogeneity measures were very similar, thus the first heterogeneity measure for each of the four assays was used.

Using the five variables, the IHC4 score, and one heterogeneity score for each assay (ER, PR, Ki-67 and HER2), the IHC4 score was modeled with each of the heterogeneity scores separately (using the cox model).

Based on the results, it was determined that the PR heterogeneity score measure was the most useful for determining time to distant recurrence, with ER adding some predictive power.

To determine if the relationship of heterogeneity score and risk was linear or not; as there is an assumption that each unit change in heterogeneity score results in the same increase in risk of distant recurrence. The data was transformed (taking square root, natural log, etc.) and the transformed variable entered into the cox model. The square root was selected as it increased the predictive ability the most.

The final modification of the measurement of heterogeneity involved taking the heterogeneity score (HET) for ER and PR, summing them and taking the square root. Heterogeneity score=square root($HET^{PR} + HET^{ER}$). The resulting HET score and the IHC4 score were entered into a cox proportional hazards model which takes the two linear variables and finds the best linear combination of the two to predict time to distant recurrence. The resulting formula is:

$$\text{Output risk score} = 1.95119 \times (\text{square root}(HET^{PR} + HET^{ER})) + 0.03114 \times IHC4$$

Figure 24:
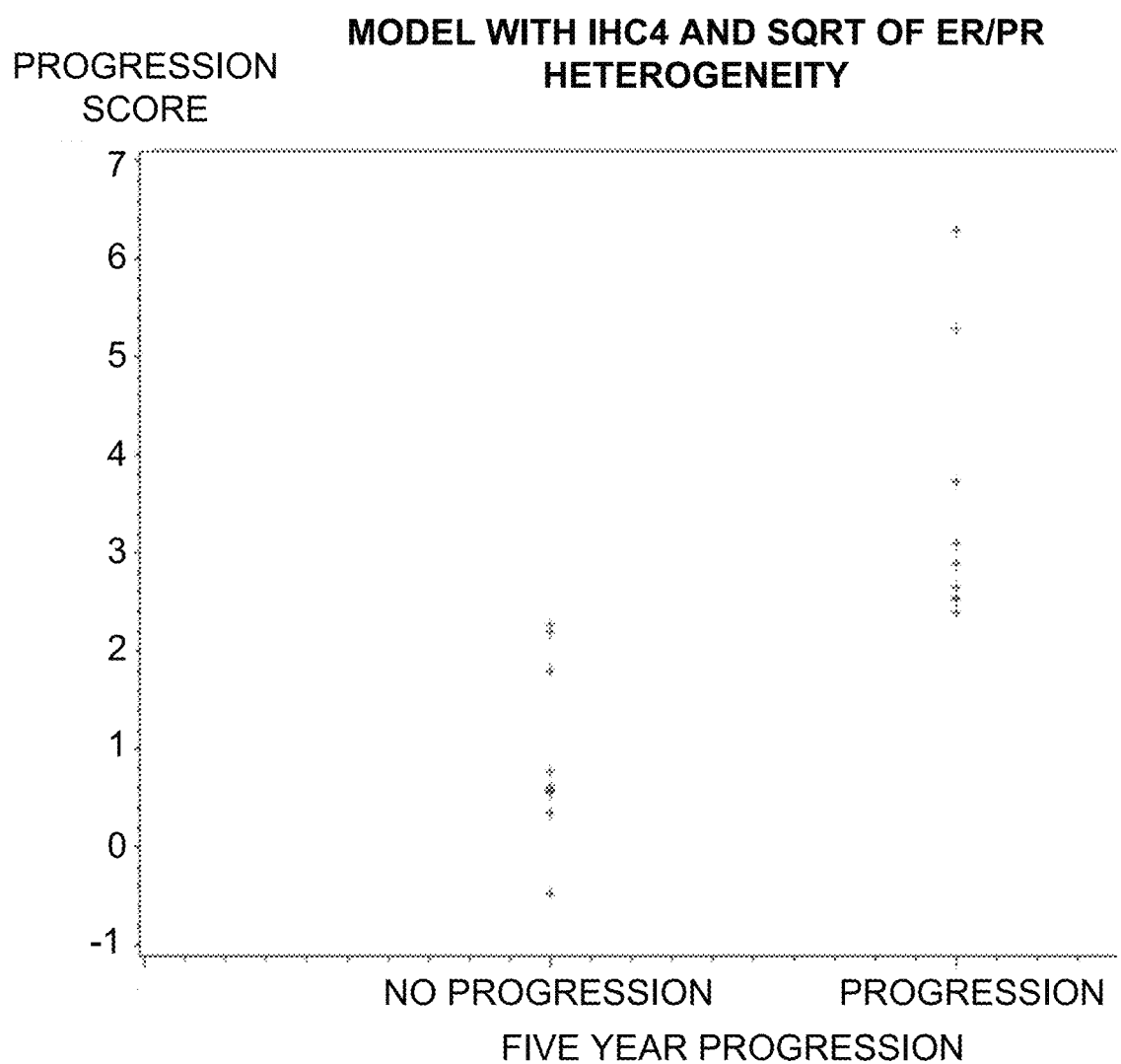
FIG. 24 is a graph showing the ability of the disclosed methods to classify a breast cancer sample as on that is more (progression) or less (no progression) aggressive. The cases shown in the graph are the same cases used to create the algorithm.

As shown in FIG. 24, this method accurately classified a breast cancer sample as one that is more (progression) or less (no progression) aggressive. The cases shown in FIG. 24 are the same cases used to create the algorithm.

Alternatives

The technologies from any example can be combined with the technologies described in any one or more of the other examples. In view of the many possible embodiments to which the principles of the disclosure may be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

The invention claimed is:
1. A method of predicting breast cancer recurrence in a human subject diagnosed with breast cancer, comprising:
   (a) obtaining one or more tissue samples from the human subject diagnosed with breast cancer, wherein the obtained one or more tissue samples are stained for the presence of at least two biomarkers for computing an immunohistochemistry combination score and stained for the presence of at least two biomarkers for computing an heterogeneity combination score;
   (b) computing the immunohistochemistry (IHC) combination score, wherein the computing of the IHC combination score comprises:
      receiving a plurality of fields of view (FOV) for computing the IHC combination score, wherein the plurality of received IHC combination score FOVs are derived from images of the one or more tissue samples stained for the presence of the at least two biomarkers for computing the IHC combination score, and wherein the plurality of received IHC combination score FOVs include at least two FOVs for each of the at least two biomarkers for computing the IHC combination score;
      measuring protein expression levels for each of the at least two biomarkers for computing the IHC combination score within each of the plurality of received IHC combination score FOVs using an automated image analysis algorithm; and
      computing the IHC combination score based on the measured protein expression levels for each of the at least two biomarkers for computing the IHC combination score;
   (c) computing the heterogeneity combination score, wherein the computing of the heterogeneity combination score comprises:
      receiving a plurality of FOVs for computing the heterogeneity combination score, wherein the plurality of received heterogeneity combination score FOVs are derived from images of the one or more tissue samples stained for the presence of the at least two biomarkers for computing the heterogeneity combination score, and wherein the plurality of received heterogeneity combination score FOVs include at least two FOVs for each of the at least two biomarkers for computing the heterogeneity combination score;
      measuring protein expression levels for each of the at least two biomarkers for computing the heterogeneity combination score within each of the plurality of received heterogeneity combination score FOVs using an automated image analysis algorithm;
      independently deriving a heterogeneity score for each of the at least two biomarkers for computing the heterogeneity combination score based on the measured protein expression levels for each of the at least two biomarkers for computing the heterogeneity combination score; and
      computing the heterogeneity combination score based on the independently derived heterogeneity scores for each of the at least two biomarkers for computing the heterogeneity combination score;
   (d) computing a breast cancer recurrence prognosis score by combining and weighting the computed immunohistochemistry combination score and the computed heterogeneity combination score;
   (e) determining whether the human subject diagnosed with breast cancer is at a high risk or at a low risk of breast cancer recurrence based on the computed breast cancer recurrence prognosis score; and
   (f) administering to the human patient an appropriate breast cancer treatment regimen if the breast cancer recurrence prognosis score is greater than the predetermined threshold value.

2. The method of claim 1, wherein the least two biomarkers for computing the IHC combination score are selected from the group consisting of an estrogen receptor (ER), a human epidermal growth factor receptor 2 (HER2), a Ki-67 biomarker, and a progesterone receptor (PR).

3. The method of claim 1, wherein the measuring of the protein expression values for each of the at least two biomarkers for computing the IHC combination score comprises calculating at least one of a percent positivity or an H-score.

4. The method of claim 1, wherein the at least two biomarkers for computing the heterogeneity combination score are selected from the group consisting of an estrogen receptor (ER), a human epidermal growth factor receptor 2 (HER2), a Ki-67 biomarker, and a progesterone receptor (PR).

5. The method of claim 4, wherein the receiving of the plurality of FOVs for the computing of the heterogeneity combination score comprises receiving at least two FOVs for each of ER, HER2, Ki-67, and PR.

6. The method of claim 1, further comprising providing a treatment recommendation for breast cancer based on the computed breast cancer recurrence prognosis score.

7. The method of claim 1, wherein the determination of the breast cancer recurrence prognosis is determined by comparing the computed breast cancer recurrence prognosis score to a predetermined threshold value.

8. The method of claim 2, wherein the IHC combinations score is an IHC4 score.

9. The method of claim 1, wherein each of the independently derived heterogeneity scores are determined by assessing a variability of the measured protein expression levels for one of the at least two biomarkers for computing the heterogeneity combination score between at least two of the received plurality of heterogeneity combination score FOVs.

10. The method of claim 1, wherein each of the independently derived heterogeneity scores are normalized prior to computing the heterogeneity combination score.

11. A method of treating a human subject diagnosed with breast cancer, comprising:
   (a) obtaining one or more tissue samples from the human subject diagnosed with breast cancer, wherein the obtained one or more tissue samples are stained for the presence of at least two biomarkers for computing an immunohistochemistry combination score and stained for the presence of at least two biomarkers for computing an heterogeneity combination score;
   (b) computing the immunohistochemistry (IHC) combination score, wherein the computing of the IHC combination score comprises:
      receiving a plurality of fields of view (FOV) for computing the IHC combination score, wherein the plurality of received IHC combination score FOVs are derived from images of of the one or more tissue samples stained for the presence of at least two biomarkers for computing the IHC combination score, and wherein the plurality of received IHC combination score FOVs include at least two FOVs for each of the at least two biomarkers for computing the IHC combination score;

measuring protein expression levels for each of the at least two biomarkers for computing the IHC combination score within each of the plurality of received IHC combination score FOVs using an automated image analysis algorithm; and computing the IHC combination score based on the measured protein expression levels for each of the at least two biomarkers for computing the IHC combination score;

(c) computing a heterogeneity combination score, wherein the computing of the heterogeneity combination score comprises:

receiving a plurality of FOVs for computing the heterogeneity combination score, wherein the plurality of received heterogeneity combination score FOVs are derived from images of the one or more tissue samples stained for the presence of at least two biomarkers for computing the heterogeneity combination score, and wherein the plurality of received heterogeneity combination score FOVs include at least two FOVs for each of the at least two biomarkers for computing the heterogeneity combination score;

measuring protein expression levels for each of the at least two biomarkers for computing the heterogeneity combination score within each of the plurality of received heterogeneity combination score FOVs using an automated image analysis algorithm;

independently deriving a heterogeneity score for each of the at least two biomarkers for computing the heterogeneity combination score based on the measured protein expression levels for each of the at least two biomarkers for computing the heterogeneity combination score; and computing the heterogeneity combination score based on the independently derived heterogeneity scores for each of the at least two biomarkers for computing the heterogeneity combination score;

(d) computing a breast cancer recurrence prognosis score by combining and weighting the computed immunohistochemistry combination score and the computed heterogeneity combination score;

(e) determining abreast cancer recurrence prognosis based on the computed breast cancer recurrence prognosis score for the subject previously treated for breast cancer; and (f) identifying an appropriate therapy for the human subject diagnosed with breast cancer based on the provided determination of breast cancer recurrence; and g) administering to the human patient an appropriate breast cancer treatment regimen if the breast cancer recurrence prognosis score is greater than the predetermined threshold value.

* * * * *